United States Patent
Helms et al.

(10) Patent No.: US 12,078,645 B2
(45) Date of Patent: Sep. 3, 2024

(54) METHOD FOR DIAGNOSING DISSEMINATED INTRAVASCULAR COAGULATION (DIC)

(71) Applicants: Hôpitaux Universitaires de Strasbourg, Strasbourg (FR); Diagnostica Stago, Asnières-sur-Seine (FR)

(72) Inventors: Julie Helms, Strasbourg (FR); Florence Toti, Strasbourg (FR); Laure Stiel, Strasbourg (FR); Laurent Mauvieux, Mundolsheim (FR); Ferhat Meziani, Oberhausbergen (FR)

(73) Assignees: HÔPITAUX UNIVERSITAIRES DE STRASBOURG, Strasbourg (FR); DIAGNOSTICA STAGO, Asnières-sur-Seine (FR)

( * ) Notice: Subject to any disclaimer, the term of this patent is extended or adjusted under 35 U.S.C. 154(b) by 1437 days.

(21) Appl. No.: 16/073,742

(22) PCT Filed: Jan. 25, 2017

(86) PCT No.: PCT/FR2017/050158
§ 371 (c)(1),
(2) Date: Jul. 27, 2018

(87) PCT Pub. No.: WO2017/129895
PCT Pub. Date: Aug. 3, 2017

(65) Prior Publication Data
US 2019/0011466 A1 Jan. 10, 2019

(30) Foreign Application Priority Data

Jan. 27, 2016 (FR) .................... 1650667
Jan. 29, 2016 (FR) .................... 1650765
Dec. 1, 2016 (FR) .................... 1661823

(51) Int. Cl.
| | |
|---|---|
| *G01N 33/53* | (2006.01) |
| *G01N 15/14* | (2006.01) |
| *G01N 33/50* | (2006.01) |
| *G01N 33/68* | (2006.01) |
| *G01N 33/86* | (2006.01) |

(52) U.S. Cl.
CPC .............. *G01N 33/86* (2013.01); *G01N 15/14* (2013.01); *G01N 33/5005* (2013.01); *G01N 33/6893* (2013.01); *G01N 2015/1486* (2013.01); *G01N 2333/70503* (2013.01); *G01N 2333/70596* (2013.01); *G01N 2800/226* (2013.01); *G01N 2800/26* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

| EP | 2587262 A2 | 10/2012 |
|---|---|---|
| WO | WO2014/184478 A1 | 11/2014 |

OTHER PUBLICATIONS

Toti, Florence., English translation of WO2014184478, Method for Diagnosing Disseminated Intraascular Coagulation, Machine translation, pp. 1-16. (Year: 2014).*
Yuan et al., DRAQ5-Based DNA content analysis of hematolymphoid cell subpopulations discriminated by surface antigens and light scatter properties, Cytometry B, Clinical Cytometry; 58B, 2004, pp. 47-52. (Year: 2004).*
Song, S. H., et al., "Neutrophil CD64 expression is associated with severity and prognosis of disseminated intravascular coagulation," Thrombosis Res. 2008;121:499-507.
Park, S. H., et al., "Sepsis affects most routine and cell population data (CPD) obtained using the Sysmex XN-2000 blood cell analyzer: neutrophil-related CPD NE-SFL and NE-WY provide useful information for detecting sepsis," Int. J. Lab. Hematol. 2015;37(2):190-198.
Sueyoshi, K., et al., "Fluorescence imaging of ATP in neutrophils from patients with sepsis using organelle-localizable fluorescent chemosensors," Ann. Intensive Care 2016;6(1):8 pp.
International Search Report and Written Opinion for PCT Patent App. No. PCT/FR2017/050158 (Apr. 11, 2017) with English translation of the ISR.

* cited by examiner

*Primary Examiner* — Gary Counts
(74) *Attorney, Agent, or Firm* — Kenealy Vaidya LLP

(57) ABSTRACT

A method and kit for-, in particular, the medical and veterinary field, predicts and/or detects disseminated intravascular coagulation (DIC) in a biological sample.

16 Claims, 8 Drawing Sheets

METHOD FOR DIAGNOSING DISSEMINATED INTRAVASCULAR COAGULATION (DIC)

CROSS REFERENCE TO RELATED APPLICATIONS

This application is a national phase filing under 35 C.F.R. § 371 of and claims priority to PCT Patent Application No. PCT/FR2017/050158, filed on Jan. 25, 2017, which claims the priority benefit under 35 U.S.C. § 119 of French Patent Application No. 1650667, filed on Jan. 27, 2016; French Patent Application No. 1650765, filed on Jan. 29, 2016; and French Patent Application No. 1661823, filed on Dec. 1, 2016; the contents of each of which are hereby incorporated in their entireties by reference.

BACKGROUND

Some embodiments relate to predicting and/or detecting disseminated intravascular coagulation (DIC) in a biological sample and to a kit for predicting and/or detecting disseminated intravascular coagulation (DIC) in a biological sample.

Some embodiments also relate to monitoring the development of disseminated intravascular coagulation (DIC) from a biological sample.

Some embodiments relate to the medical and veterinary field.

In the description below, the references between square brackets ([ ]) refer to the reference list at the end of the text.

RELATED ART

Septic shock is a syndrome characterized by an inflammatory reaction of the host in response to a pathogenic agent, responsible for hypotension that is resistant to volume expansion and requiring the introduction of vasopressors (noradrenalin) and accompanied by organ failures.

Coagulation is activated constantly during septic shock and participates in the host's defences. However, this activation may be "dysregulated" with thrombocytopenia, leucocyte and endothelial stimulation and also consumption of coagulation factors and coagulation inhibitors, being reflected by microthromboses and responsible for disseminated intravascular coagulation (DIC). The link between DIC, severity and multiple organ failure has been known for a long time and is the rationale behind the use of anticoagulant treatments during septic shock, in addition to etiological and organ failure treatments. However, clinical studies relating to treatments having an effect on coagulation—which have never or rarely specifically targeted patients with DIC—have proved to be disappointing since they do not make it possible to improve or enhance patients' prognosis.

In France, 80 000 cases of sepsis are observed each year, with sepsis being defined as a systemic inflammatory response developed by the body in response to invasion by a pathogenic microorganism, and reflected by hypoperfusion of the organs and an oxygen debt, possibly developing into presentation of multiple organ failure. Arterial hypotension is persistent in these cases despite suitable vascular filling, and may require the use of vasopressors (noradrenaline, adrenaline). It is therefore a serious, and relatively common, disease.

This state is associated with intensive cellular activation via the induction of proinflammatory cytokines and phenotypic modifications of the vascular endothelium, which then assumes a pro-adhesive, proinflammatory and prothrombotic nature.

It has been shown in the related art that, after invasion by a pathogenic agent, the host's response involves the innate immune system and the adaptive immune system. The innate immune system constitutes the first line of defence by releasing a large number of chemokines and cytokines (Aziz et al., 2013).

Polynuclear neutrophils (PNNs) are cells of the innate immune system. These cells were long considered to be cells having the sole function of phagocytosing extracellular pathogens. Over recent years, the development of knowledge on physiology and the place of PNNs has progressed toward a more complex view combining innate immunity, adaptive immunity and hemostasis (Mócsai, 2013). While PNNs play a major role in antibacterial defense via phagocytosis, it has been demonstrated since the start of the 2000s that they also play a role in protecting against intracellular germs (viruses, mycobacteria) and in regulating the adaptive immune response, in particular by interacting with the B lymphocytes of the marginal zone within the spleen. Thus, PNNs are capable of releasing the content of their nucleus, DNA and histones, forming a network which supports enzymes such as myeloperoxidase (MPO) or elastase. These structures, described for the first time in 2004, are referred to as NETs (Neutrophil Extracellular Traps) and are capable of capturing pathogens in their macromolecular network (Brinkmann et al., 2004). Two mechanisms of NETosis have been described: one leads to cell suicide and lasts for a few hours, and the other, "vital" NETosis, which is quicker, enables the survival of the PNN in anucleated form which is capable of phagocytosis, a function which does not depend on the synthesis of new proteins and hence on the presence of a nucleus (Fuchs et al., 2007).

The two mechanisms are accompanied by morphological modifications of the PNNs, described by electron microscopy following in vitro NETosis induction by PMA or phorbol-myristate-acetate (Brinkmann and Zychlinsky, 2012). First of all, the chromatin decondenses, the nucleus loses its lobules, the cytoplasm degranulates and the NETs are expelled by the cell. The vital NETosis pathway appears to be involved during infections by Gram-positive bacteria. The NETs are released from vesicles containing decondensed chromatin and antibacterial proteins.

The NETs perform an antimicrobial function by trapping bacteria and mycetes, but could also have a role in thrombi formation. Thus, NETs could be a major player in a new concept referred to as immunothrombosis (Kessenbrock K, et al., 2015; Engelmann et Massberg, PMID 2013).

At the current time, the speed of the process of NETosis, the focusing thereof at the site of infection and the degradation of the DNA by circulating nucleases are obstacles to direct in vivo detection in circulating blood. However, there are indirect markers of NETosis, especially the combination of high levels of circulating nucleosomes, citrullinated histones and MPOs (Abrams et al., 2013), (Kessenbrock et al., 2009). NETosis has been able to be associated, via these markers, with various pathological conditions, especially thrombotic, infectious, cancerous or autoimmune pathological conditions (Kessenbrock et al., 2009)° (Demers et al., 2012).

NETs therefore not only play a role in the host's defense mechanisms, but also participate in the interaction between inflammation and coagulation during infectious processes (Branzk and Papayannopoulos, 2013).

There are processes for detecting leukocytes and neutrophils using flow cytometry, as described in the United States patent application published under the number US 2013/0101996, in order to determine for example if the body is in the process of host defense.

Two biological scores combining blood parameters that are accessible in the related art have been proposed for diagnosing DIC. One of the difficulties in developing scores lies in the fact that there is not currently a consensus on the "biological definition" of DIC. The first detection test, described in 2001, comes from the International Society for Thrombosis and Haemostasis (ISTH), and the second test came from the Japanese Association for Acute Medicine (JAAM) in 2005 and was revised in 2006.

The ISTH score is based on the presence of severe thrombocytopenia, on a reduction in the amount of prothrombin (lengthening of the Quick prothrombin time), on consumption of the fibrinogen and on increased D-dimers, markers of fibrinolysis. It makes it possible to diagnose DICs occurring during neoplastic diseases, trauma, or obstetric pathology, but appears insufficient during septic shock, due to the importance of inflammatory syndrome with thrombocytosis, elevated fibrinogen and the presence of D-dimers. It therefore appears ill-suited to detecting DIC during a septic shock.

The JAAM score was developed in order to diagnose DIC during septic shock, and does not take fibrinogen as a diagnostic criterion, while using more "coherent" threshold values in the context of sepsis for D-dimers and platelets. These differences have led to discussions by the DIC committee of the ISTH to redefine the DIC entity by separating obstetric, trauma-based, septic or oncological coagulopathies.

However, these scores can only be calculated and used from particular samples and may require a significant period of time to obtain results, thereby generating significant costs and delays in treatment.

In addition, there is currently no process that makes it possible to safely and systematically detect a DIC. There is also no process and/or method that makes it possible to predict the occurrence, for example from a biological sample, of disseminated intravascular coagulation.

There is no process in the related art that makes it possible to determine, in an individual with septic shock, whether the septic shock will trigger/present disseminated intravascular coagulation in the near future. On the other hand, there is a process capable of establishing a prediction of a negative DIC diagnosis in an individual having septic shock. This is especially a score combining 3 parameters: The concentration of circulating membrane microparticles exposing phosphatidylserine and the CD105 antigen, the platelet count and the prothrombin level, with a specificity of 71.2%, sensitivity of 71.0%, and a negative predictive value of 93.1%. Although this process is effective, it is not technologically easy and quick to carry out.

SUMMARY

There is therefore a real need to find a process and/or method that overcomes these flaws, drawbacks and obstacles of the related art, in particular a simple, quick and effective process making it possible to detect DIC, in order to improve or enhance the vital prognosis of individuals and thereby reduce treatment costs for the individuals.

Some embodiments therefore attempt to address or overcome the drawbacks of the related art by providing a process for predicting and/or detecting disseminated intravascular coagulation (DIC) from a biological sample including a step of detecting and/or measuring the concentration and/or content of at least one biological marker.

In the present document, "biological marker" is intended to mean at least one biological marker selected from the group including neutrophils, platelets and phosphatidylserine-exposing blood microparticles.

According to some embodiments, the at least one selected biological marker may be detected by any suitable process known to those of ordinary skill in the art.

According to some embodiments, the content of the at least one selected biological marker may be measured by any suitable process known to those of ordinary skill in the art.

According to some embodiments, the concentration of the at least one selected biological marker may be measured by any suitable process known to those of ordinary skill in the art.

In the present document, "neutrophils" is intended to mean neutrophil granulocytes or polynuclear neutrophils (PNNs) which are blood cells belonging to the white line (leukocytes), which therefore have a role in the immune system.

In the present document, the fluorescence of the neutrophils may be measured by any suitable process known to those of ordinary skill in the art.

This may be, for example, a process using a label for the neutrophils, for example a fluorescent label. The fluorescence may be measured by any suitable process known to those of ordinary skill in the art. This may be for example a flow cytometry process, based on the recognition of fluorochromes and/or fluorescent probes. It may be for example a process including labelling neutrophils including the use of a fluorochrome. It may for example be a process including the application of a fluorochrome to a sample, for example a blood sample, after a step of lysis of the red blood cells by a first reactant which may also act on the leukocyte membranes by permeabilizing same, thereby making it possible to attach the fluorochrome.

In the present document, "fluorochrome" is intended to mean an agent without membrane permeation, based or not based on polymethine, which binds to nucleic acids. It may advantageously be a fluorochrome which only diffuses into the cytoplasm through the permeabilized and fixed membrane, for example the permeabilized and fixed leukocyte membrane.

The fluorescent probes may for example be intercalators which are inserted between the DNA bases, or probes specific to citrullinated histones, for example antibodies, or probes specific to a post-translational modification or conformation of the histones, of the nucleosomes or any DNA structural protein or protein that attaches to DNA in association with DNA decompaction or by NETosis, or a specific nuclear sequence that is accessible to labelling during NETosis, or probes targeting DNA breakages or probes measuring the early phases of apoptosis such as modifications to the plasma membrane or mitochondrial membrane.

They may for example be molecules selected from the group including DNA intercalators, decompaction probes or markers of enzymatic activity associated with DNA during NETosis, whether insolubilized or not and on any type of support, combined or not.

They may for example be propidium iodide, antibodies, for example anti-citrullinated histone, anti-DNA antibodies, fluorescent substrates for the activity of proteins associated with decompacted DNA such as leukocyte elastase, PR3 or myeloperoxidase, measuring DNA modification by TUNEL effect, by flow cytometry, measuring extramembrane annexin V, or DiOC6 (3,3'-dihexyloxacarbocyanine iodide) incorporation.

The fluorochrome and/or fluorescent probe may be any suitable fluorochrome and/or fluorescent probe known to those of ordinary skill in the art. It may be, for example, a commercially available fluorochrome and/or fluorescent probe, for example those sold by Thermofischer under the commercial references Syto40, DIOC6(3) and Thiazole Orange. Those of ordinary skill in the art, due to their general knowledge, will know how to choose the suitable fluorochrome and/or probe for labelling neutrophils.

In addition, those of ordinary skill in the art, due to their general knowledge, know the different leukocyte populations and will know how to identify them, for example during flow cytometry, as a function of their particle size distribution or their size.

When the process for measuring the fluorescence of polynuclear neutrophils is a process using an intercalating fluorochrome, for example a flow cytometry process, this may for example be Syto40, propidium iodide and the Gallios (Beckman-Coulter) or FACS-Canto (Becton-Dickinson) flow cytometer and/or any other flow cytometer equipped for example with 3 lasers including one violet (405 nm) and one blue (488 nm) laser, with logarithmic gain setting, with for example the fluorescence of SYTO 40 measured on a detector coupled with the violet (405 nm) laser, and combined with a passband filter centered around 450-460 nm, the other lasers being used for the identification of the leukocytes and neutrophils for example by anti-CD45-FITC and anti-CD49d antibodies.

According to some embodiments, "fluorescence intensity" is intended to mean any signal measured at the re-emission wavelength of the fluorophore after excitation for example at 630 nm. The fluorescence intensity is proportional to the state of decompaction of the DNA.

In the present document, the fluorescence of the neutrophils may be measured by any device known to those of ordinary skill in the art that is suitable for some embodiments. This may for example be a device sold by Sysmex, by Socimed, or by Alere. It may for example be the Sysmex XN automated analyzer.

The applicants have demonstrated that the measurement of the fluorescence of the neutrophils from a biological sample, for example a blood sample, makes it possible to determine the presence of DIC in an individual with septic shock and/or to identify an individual capable of developing DIC.

A subject of some embodiments is an in-vitro process for predicting and/or detecting disseminated intravascular coagulation (DIC) from a first biological sample including a step of measurement of neutrophil fluorescence.

In addition, a subject of some embodiments is an in-vitro process for detecting disseminated intravascular coagulation (DIC) including a measurement, from a first biological sample, of neutrophil fluorescence.

In the present document, "biological sample" is intended to mean any sample obtained from mammals, for example a mammal selected from the group including the orders Monotremata, Didelphimorphia, Paucituberculata, Microbiotheria, Notoryctemorphia, Dasyuromorphia, Peramelemorphia, Diprotodontia, Tubulidentata, Sirenia, Afrosoricida, Macroscelidea, Hyracoidea, Proboscidea, Cingulata, for example the armadillo, Pilosa, Scandentia, Dermoptera, Primates, Rodentia, Lagomorpha, Erinaceomorpha, Soricomorpha, Chiroptera, Pholidota, Carnivora, Perissodactyla, Artiodactyla and Cetacea. It may for example be a human or an animal. It may for example be a livestock animal, a pet, a threatened animal species or any other animal.

According to some embodiments, the biological sample may be a blood sample.

According to some embodiments, the biological sample may originate from a mammal with septic shock or a risk of septic shock.

According to some embodiments, the detection process may also include a step of comparing the measured fluorescence intensity with a reference fluorescence value.

According to some embodiments, the reference fluorescence value may be the fluorescence intensity of neutrophils measured in a subject, or the mean concentration value measured in a group of reference healthy subjects.

In the present document, "reference healthy subject" is intended to mean a mammal, for example a human being, that has not been subject to an infection, shock, hemorrhage, septic shock and/or any other attack on the body capable of leading to disseminated intravascular coagulation as defined above.

According to some embodiments, "group of reference subjects" is intended to mean a group making it possible to define a reliable reference value. It may for example be a group including at least 2 reference subjects as defined above, for example at least 10, at least 40, at least 60, at least 100 reference subjects. It may for example be a group including from 30 to 500 subjects, from 40 to 200, from 45 to 110 reference subjects.

According to some embodiments, the neutrophil fluorescence reference value $R_{Neut\ SFL}$ or Rneutfl may also be a value obtained by analysis of an ROC curve obtained from statistical analysis of values obtained from a reference subject and/or a group of reference subjects. The reference value may be determined, for example obtained, via an ROC curve as described in Stiel et al. "Neutrophil Fluorescence: A New Indicator of Cell Activation During Septic Shock-Induced Disseminated Intravascular Coagulation." Crit Care Med. 2016; 44(11):e1132-e1136.

According to some embodiments, when the neutrophil fluorescence is measured with a device sold by Sysmex, for example the Sysmex XN automated analyzer, the reference value for neutrophil fluorescence, $R_{Neut\ SFL}$ or Rneutfl obtained via an ROC curve as described in Stiel et al. "Neutrophil Fluorescence: A New Indicator of Cell Activation During Septic Shock-Induced Disseminated Intravascular Coagulation." Crit Care Med. 2016; 44(11):e1132-e1136, may be a fluorescence of greater than 57 arbitrary units.

Advantageously, the applicants have demonstrated that when the measured fluorescence value is greater than the reference value, the process according to some embodiments makes it possible to detect and/or predict disseminated intravascular coagulation.

Advantageously, the applicants have also demonstrated that the process for detecting DIC including determining/measuring neutrophil fluorescence enables detection of DIC with a sensitivity of greater than or equal to 91% and a specificity of greater than or equal to 81%.

According to some embodiments, the process for predicting and/or detecting disseminated intravascular coagulation may also include a step of measurement, from a second biological sample, of the concentration $RO_{CD105}$ of membrane microparticles bearing the cluster of differentiation 105 (CD105) and exposing phosphatidylserine.

In the present document, "phosphatidylserine-exposing blood microparticles" is intended to mean phosphatidylserine-exposing microparticles of the plasma membrane. These may for example be membrane microparticles released for example into the vascular space from cells, for example endothelial cells, platelets, monocytes, granulocytes or polynuclear cells (neutrophils, eosinophils or basophils) or circulating precursors thereof, erythrocyte cells, lymphocytes or cells of non-vascular origin, exposing phosphatidylserine. For example, the membrane microparticles may have a size, that is to say an individual diameter, of between 50 nm and 1 μm, and expose phosphatidylserine. For example, the membrane microparticles may have a tissue factor activity or a fibrinolytic activity.

The concentration of membrane microparticles bearing cluster of differentiation may be measured by any suitable process known to those of ordinary skill in the art. This may for example be a flow cytometry process based on the recognition of fluorescent probes, for example labelled antibodies, protein or lipid probes, whether fixed to beads or not, or even probes recognizing genetic material included in the microparticles, such as miRNAs. The probes may also be specific for phosphatidylserine (PhtdSer), for example annexin 5 or any other derivative of annexin obtained by molecular engineering, for example diannexins. The probes may also, for example, recognize membrane lipids and the degrees of compaction thereof, for example lipid probes having longer or shorter carbon-based chains. The protein probes may for example be antibodies detecting clusters of differentiation at the surface of the microparticles, or detecting any other protein or enzyme located at the surface of the microparticles or in the microparticle, such as actin, metalloproteases, protein receptors with enzymatic activity, for example tissue factor or uPAR, cytokines and interleukins. The concentration of the microparticles may also be measured by quantitative assay of total lipids or total proteins or by of the Tunable Resistive Pulse Sensing technique. The concentration of membrane microparticles may also be measured for example via a prothrombinase test as described in Hugel B, Zobairi F, Freyssinet J M. Measuring circulating cell-derived microparticles. J Thromb Haemost. 2004 October; 2(10):1846-7 [12]. Briefly, in this process, the blood coagulation factors and the calcium concentration are determined such that PhtdSer is the limiting parameter in the generation of soluble thrombin from exogenous prothrombin added to the reaction medium. The results are expressed in nanomolar of PhtdSer equivalent (nM eq. PhtdSer) by reference to a calibration curve produced with liposomes of known composition and concentration, as described in Hugel B, Zobairi F, Freyssinet J M. "Measuring circulating cell-derived microparticles", J Thromb Haemost. 2004 October; 2(10):1846-7 [12]. The concentration of the microparticles may also be measured, for example, by measuring the tissue factor activity. Briefly, the process uses specific coagulation factors of the complex referred to as tenase, and assays the formation of factor Xa from factor X added to the reaction medium, as described in Aupeix K, et al. "The significance of shed membrane particles during programmed cell death in vitro, and in vivo, in HIV-1 infection." J Clin Invest 1997; 99(7): 1546-54. [13]. The activity carried by the TF+MPs is related to a calibration curve of known concentration of tissue factor. The concentration obtained is expressed in pmol per liter of tissue factor activity. The concentration of the membrane microparticles may also be measured for example by a chronometric method based on beads covered with a capture, for example an antibody, enabling the identification (phenotype) of the microparticles and the measurement of a coagulation time after addition of a plasma devoid of phospholipids. In this method, the coagulation time is dependent on the amount of anionic phospholipids (PhtdSer) provided by the MPs specifically captured beforehand by the beads. Calibration of the chronometric test using a solution of liposomes of known concentration in order may optionally be carried out, and makes it possible to convert the chronometric result (seconds) into procoagulant activity (nM eq. Phtd Ser). This may be carried out for example by of automated analyzers of the STAR range from Stago.

According to some embodiments, the second biological sample is a biological sample as defined above.

According to some embodiments, the second biological sample may be identical to or different from the first biological sample.

According to some embodiments, the first and second biological samples may be a single and the same sample.

According to some embodiments, the first and/or second biological sample may originate from a mammal with septic shock.

According to some embodiments, the process for predicting and/or detecting DIC may also include a step of comparing the measured concentration $R0_{CD105}$ with a reference value $R_{CD105}$.

According to some embodiments, the reference value $R_{CD105}$ may be the value of the concentration of microparticles bearing the cluster of differentiation CD105 measured in a subject, or the mean concentration value measured in a group of reference healthy subjects.

According to some embodiments, the reference healthy subject or the group of reference healthy subjects is as defined above.

According to some embodiments, the reference value $R_{CD105}$ may also be a value obtained by analysis of an ROC curve.

According to some embodiments, the reference value $R_{CD105}$ may be a concentration of microparticles bearing the cluster of differentiation of greater than 0.65 nM of PhtdSer or PS equivalent.

Advantageously, the applicants have demonstrated that a measured concentration of microparticles bearing the cluster of differentiation CD105 that is greater than the reference value, according to the process of some embodiments, makes it possible to detect and/or predict disseminated intravascular coagulation (DIC).

Advantageously, the applicants have demonstrated that the process for detecting DIC, also including determining the concentration $R0_{CD105}$, enables detection with a sensitivity of greater than or equal to 69% and a specificity of greater than or equal to 48%.

According to some embodiments, the process for predicting and/or detecting disseminated intravascular coagulation (DIC) may also include a step of measurement, from a third biological sample, of the platelet concentration R0Plt.

In the present document, "platelets" is intended to mean blood platelets or thrombocytes formed by fragmentation of megakaryocytes.

According to some embodiments, the third biological sample is a biological sample as defined above.

According to some embodiments, the third biological sample may be identical to or different from the first and/or second biological sample.

According to some embodiments, the first and third biological samples may be the same sample.

According to some embodiments, the second and third biological samples may be the same sample.

According to some embodiments, the first, second and third biological samples may be the same sample.

According to some embodiments, the platelet concentration in a sample may be measured by any suitable process known to those of ordinary skill in the art. This may for example be the processes described by McNair et al, JECT. 2015; 47:113-118 and/or a process, for example automated by virtue of a Coulter-type counter using electrical impedance to derive a platelet concentration therefrom. Indeed, the passage of cells suspended in an electrolyte, modifying the electrical resistance between two electrodes, generates a variation in impedance that is recorded in the form of an impulse correlated to the passage of the cells for which it is sought to establish the concentration (Coulter principle).

According to some embodiments, the process for predicting and/or detecting DIC may also include a step of comparing the measured concentration R0Plt with a reference value RPlt.

According to some embodiments, the reference value RPlt may be the value of the platelet concentration measured in a reference healthy subject, or the mean of the concentration values measured in a group of reference healthy subjects.

According to some embodiments, the reference healthy subject or the group of reference healthy subjects is as defined above.

According to some embodiments, the reference value RPlt may also be a value obtained by analysis of an ROC curve.

According to some embodiments, the reference value RPlt may be a content of platelets, for example equal to 127 g/l.

Advantageously, the applicants have demonstrated that the process for detecting DIC, including determining the concentration RPlt, enables detection with a sensitivity of greater than or equal to 68% and a specificity of greater than or equal to 90%.

According to some embodiments, the process for predicting and/or detecting disseminated intravascular coagulation (DIC) may also include a step of measuring the prothrombin level RoTP.

According to some embodiments, the process for predicting and/or detecting disseminated intravascular coagulation (DIC) may also include a step of measurement, from a fourth biological sample, of the prothrombin level ROTP.

According to some embodiments, the fourth biological sample is a biological sample as defined above.

According to some embodiments, the fourth biological sample may be identical to or different from the first, second and/or third biological sample.

According to some embodiments, the first and fourth biological samples may be a single and the same sample.

According to some embodiments, the second and fourth biological samples may be the same sample.

According to some embodiments, the third and fourth biological samples may be a single and the same sample.

According to some embodiments, the first, second and fourth biological samples may be a single and the same sample.

According to some embodiments, the first, third and fourth biological samples may be a single and the same sample.

According to some embodiments, the second, third and fourth biological samples may be a single and the same sample.

According to some embodiments, the first, second, third and fourth biological samples may be a single and the same sample.

According to some embodiments, the prothrombin level in a sample may be measured by any suitable process known to those of ordinary skill in the art. This may for example be the process described in Delabranche et al., CCMED 2016 and/or the process including for example an assay of factor II by colorimetry and/or via the use of an automated analyzer of the STAGO STA-R Evolution type, using routine, suitable, commercially available reactants.

According to some embodiments, the process for predicting and/or detecting DIC may also include a step of comparing the measured prothrombin level ROTP with a reference value RTP.

According to some embodiments, the reference value RTP may be the value of the prothrombin level ROTP measured in a reference healthy subject, or the mean of the concentration values measured in a group of reference healthy subjects.

According to some embodiments, the reference healthy subject or the group of reference healthy subjects is as defined above.

According to some embodiments, the reference value ROTP may also be a value obtained by analysis of an ROC curve.

According to some embodiments, the reference value RTP may be a prothrombin level of less than 58%.

Advantageously, the applicants have demonstrated that when the measured prothrombin level is less than the reference value, the process according to some embodiments makes it possible to detect and/or predict disseminated intravascular coagulation (DIC).

Advantageously, the applicants have also demonstrated that the process for detecting DIC, including determining the concentration $Ro_{TP}$, enables detection with a sensitivity of greater than or equal to 73% and a specificity of greater than or equal to 60%.

Advantageously, the applicants have also demonstrated that the process for detecting DIC, including determining the combination of fluorescence and CD105, platelets and prothrombin level, enables detection with a sensitivity of greater than or equal to 76% and a specificity of greater than 86%.

In other words, the process according to some embodiments, including, from at least one biological sample, the measurement of neutrophil fluorescence, for example using Sysmex XN automated analyzers, the measurement of the platelet concentration, the prothrombin level and membrane microparticles including the cluster of differentiation 105 (CD105), enables detection with a sensitivity of greater than or equal to 76% and a specificity of greater than or equal to 86%.

Advantageously, the applicants have also demonstrated that the process for detecting DIC, including determining the combination of neutrophil fluorescence, platelet count and prothrombin level, enables detection with a sensitivity of greater than or equal to 66% and a specificity of greater than or equal to 85%.

In the present document, the measured neutrophil fluorescence value R0Neut SFL is independently denoted R0neutfl, the value Vneutfl may also be denoted Vneutsfl and the reference value $R_{Neut\ SFL}$ is independently denoted RNeutfl.

Another subject of some embodiments is an in vitro process for detecting and/or monitoring the development of disseminated intravascular coagulation (DIC) from a biological sample, including the following steps:

a. measuring neutrophil fluorescence $R_{0neutfl}$ b. comparing the measured neutrophil fluorescence value R0neutfl with a reference value Rneutfl
c. measuring the concentration $R_{0CD105}$ of membrane microparticles bearing the cluster of differentiation 105 (CD105)
d. comparing the measured value $R_{0CD105}$ with a reference value $R_{CD105}$
e. measuring the platelet concentration RoPlt
f. comparing the measured value RoPlt with a reference value RPlt
g. measuring the prothrombin level RoTP
h. comparing the measured value RoTP with a reference value RTP
i. assigning a neutrophil fluorescence value Vneutfl equal to 1 if R0neutfl is greater than the value Rneutfl or a value Vneutfl equal to 0 if R0neutfl is less than the value Rneutfl
j. assigning a value $V_{CD105}$ equal to 1 if $R_{0CD105}$ is greater than the value $R_{CD105}$ or a CD105 value equal to 0 if $R_{0CD105}$ is less than the value $R_{CD105}$
k. assigning a value $V_{Plt}$ equal to 1 if RoPlt is less than the value RPlt or a value $V_{Plt}$ equal to 0 if RoPlt is greater than the value RPlt
l. assigning a value VTP equal to 1 if RoTP is less than the value RTP or a value VTP equal to 0 if RoTP is greater than the value RTP
m. calculating the score S1 according to the following formula:

$$S1=\varepsilon+Vneutfl \times \alpha+V_{CD105} \times \beta+V_{platelets} \times \Omega+V_{TP} \times \theta$$

wherein ε is from −0.708 to 2.280, for example equal to 0.786, a is from 0.152 to 1.928, for example equal to 1.040, p is from 0.154 to 1.549, for example equal to 0.851, 0 is from −0.016 to −0.005, for example equal to −0.010, 6 is from −0.036 to 0.001, for example equal to −0.017.

In addition, the applicants have shown that, when the value of S1 is greater than −0.47, the process advantageously enables prediction with a sensitivity of greater than or equal to 76% and a specificity of greater than or equal to 86%.

In other words, the scores obtained may be correlated with the future outcome for the mammal from which the biological sample originates.

According to some embodiments, the process may include, alternatively and/or additionally to the calculation of the S1 score, a step n. of calculation of the S2 score, as follows:
n. Calculating the score S2 according to the following formula:

$$S2=\varepsilon+Vneutfl \times \alpha+V_{platelets} \times \Omega+V_{TP} \times \theta$$

wherein ε is from 0.381 to 3.070, for example equal to 1.726, α is from 0.209 to 1.910, for example equal to 1.060,) is from −0.015 to −0.005, for example equal to −0.10, and 6 is from −0.040 to −0.004, for example equal to −0.022.

In addition, the applicants have demonstrated that, when the value of S2 is greater than 0.16, the process advantageously enables prediction of DIC with a sensitivity of greater than or equal to 66% and a specificity of greater than or equal to 95%.

In other words, the applicants have clearly demonstrated that the scores obtained can be correlated with the future outlook of the mammal from which the biological sample originates, and advantageously make it possible to detect DIC.

Another subject of some embodiments is a process for detecting and/or monitoring the development of disseminated intravascular coagulation (DIC) from a biological sample, including the following steps:
a. measuring the concentration $R_{0CD105}$ of membrane microparticles bearing the cluster of differentiation 105 (CD105)
b. comparing the measured value $R_{0CD105}$ with a reference value $R_{CD105}$
c. measuring the platelet concentration RoPlt
d. comparing the measured value RoPlt with a reference value RPlt
e. measuring the prothrombin level RoTP
f. comparing the measured value RoTP with a reference value RTP
g. assigning a value $V_{CD105}$ equal to 1 if $R_{0CD105}$ is greater than the value $R_{CD105}$ or a value $V_{CD105}$ equal to 0 if $R_{0CD105}$ is less than the value $R_{CD105}$
h. assigning a value $V_{Plt}$ equal to 1 if RoPlt is less than the value RPlt or a value $V_{Plt}$ equal to 0 if RoPlt is greater than the value RPlt
i. assigning a value $V_{TP}$ equal to 1 if RoTP is less than the value RTP or a value $V_{TP}$ equal to 0 if RoTP is greater than the value RTP
j. calculating the score S3 according to the following formula: $S3=\varepsilon+\alpha \times V_{CD105}+\beta \times V_{Plt}+\gamma \times V_{TP}$
wherein ε is between 0.686 and 2.830, for example equal to 1.758, α is between 0.180 and 0.785, for example equal to 0.483, β is between −0.018 and −0.009, for example equal to −0.014, and γ is between −0.027 and 0.001, for example equal to −0.013.

The applicants have demonstrated that, when the value of S3 is greater than 0.03, the process advantageously enables prediction of DIC with a sensitivity of greater than or equal to 67% and a specificity of greater than or equal to 94%.

In other words, the scores obtained may be correlated with the future outcome for the from which the biological sample originates.

In other words, the scores obtained may be correlated with the future outcome for the from which the biological sample originates.

Another subject of some embodiments is an examination for detecting disseminating intravascular coagulation (DIC) according to some embodiments, including methods for measuring neutrophil fluorescence and neutrophil concentration.

The methods for measuring neutrophil concentration and/or fluorescence are as defined above.

Another subject of some embodiments is an in vitro process for detecting disseminated intravascular coagulation (DIC) including a step of morphological analysis of the neutrophils on a blood smear.

In other words, the process may additionally include a step of morphological analysis of the neutrophils, for example on a blood smear.

According to some embodiments, the process for predicting and/or detecting DIC may also include a step of comparison of the morphology of the neutrophils, for example on a blood smear, with the morphology of neutrophils observed, for example from a blood smear, from a subject or group of reference healthy subjects.

According to some embodiments, the reference healthy subject or the group of reference healthy subjects is as defined above.

According to some embodiments, the morphological analysis may be carried out from a blood smear. According to some embodiments, a blood smear may be obtained by any suitable process known to those of ordinary skill in the art. This may for example be the process described in Stiel et al., "Neutrophil Fluorescence: A New Indicator of Cell Activation During Septic Shock-Induced Disseminated Intravascular Coagulation." Crit Care Med. 2016; November; 44(11):e1132-e1136 enabling especially analysis by visual observation, by virtue of an optical microscope following May-Grünwald Giemsa or Wright staining performed on a slide.

According to some embodiments, the step of analysis or comparison of the morphology of the neutrophils may include the observation of at least one parameter selected from the group including the chromatin condensation of the neutrophils, the granules of the neutrophils and the vacuoles of the neutrophils.

According to some embodiments, the step of analysis or comparison of the morphology of the neutrophils may include the observation of at least two parameters selected from the group including the chromatin condensation of the neutrophils, the granules of the neutrophils and/or the vacuoles of the neutrophils.

According to some embodiments, the step of analysis or comparison of the morphology of the neutrophils may include the observation of the chromatin condensation of the neutrophils, the granules of the neutrophils and/or the vacuoles of the neutrophils.

According to some embodiments, the chromatin of the neutrophils may be condensed or decondensed. Those of ordinary skill in the art, due to their general knowledge, know how to determine the condensation or decondensation of the neutrophil chromatin.

According to some embodiments, the observation of the granules of the neutrophils may include determining the number and/or density of the granules of the neutrophils. Those of ordinary skill in the art, due to their general knowledge, know the normal density and morphological appearance of the granules of the neutrophils.

According to some embodiments, the observation of the vacuoles may include determining the presence or absence of neutrophil vesicles on the smear. Those of ordinary skill in the art, due to their general knowledge, know how to determine the presence or absence of vacuoles on neutrophils.

According to some embodiments, the process may also include a step of comparison between the morphology, for example abnormal morphology, of the neutrophils originating from a biological sample, and the normal morphology of the neutrophils in a healthy subject, and establishing a cytological abnormality score.

According to some embodiments, the morphological analysis may for example be carried out by biological sample on 1 to 1000 neutrophils, for example on 1 to 100 neutrophils. For example, when the morphological analysis is carried out on a blood smear, it may be carried out on 1 to 100 neutrophils.

Another subject of some embodiments is a process for detecting and/or monitoring the development of disseminated intravascular coagulation (DIC) from a biological sample, also including the following steps:
  observation of the chromatin condensation of the neutrophils,
  observation of the number and/or density of the granules of the neutrophils,
  observation of the vacuoles of the neutrophils.

Other advantages may become apparent to those of ordinary skill in the art on reading the examples below, illustrated by the appended figures, given by way of illustration.

BRIEF DESCRIPTION OF THE FIGURES

FIG. 2A represents a box plot of the mean concentration of the membrane microparticles as phosphatidylserine equivalent (y-axis) during septic shock (gray) or not during septic shock (white). The results represented are the total membrane microparticle concentration (PhtdSer-microparticles). FIG. 2B represents the concentrations of leukocyte-derived membrane microparticles (CD11a-microparticles) related to circulating leukocytes, and FIG. 2C represents endothelial cell-derived membrane CD105 microparticles-microparticles and FIG. 2D represents endothelial cell-derived membrane CD31 microparticles-microparticles.

FIG. 6 A represents box-and-whisker plots of the mean fluorescence of neutrophils ("NEUT-FL (MFI)") labelled with the intercalator Syto40 in septic patients with DIC ("DIC") (n=5) and in non-septic patients ("non sepsis") (n=11) and also histograms of the corresponding fluorescences ("PNN non sepsis" and "PNN DIC", respectively).

FIG. 6 B I represents scattergrams (SSC/FSC) of all the cells and the neutrophil fluorescence plots before (TO) and after myeloperoxidase labelling at the surface of neutrophils undergoing NETosis and after incubation for 30 minutes with ionomycin (T 30).

FIG. 6 B II represents scattergrams (SSC/FSC) of all the cells and the neutrophil fluorescence plots before (TO) and after intracellular myeloperoxidase labelling at the surface of neutrophils undergoing NETosis and after incubation for 30 minutes with ionomycin (T 30).

FIG. 6 C I represents scattergrams (SSC/FSC) of all the cells and the neutrophil fluorescence plots before (TO) and after citrullinated histone labelling at the surface of neutrophils undergoing NETosis and after incubation for 30 minutes with ionomycin (T 30).

FIG. 6 C II represents scattergrams (SSC/FSC) of all the cells and the neutrophil fluorescence plots before (TO) and after citrullinated histone labelling at the surface of neutrophils undergoing NETosis and after incubation for 30 minutes with ionomycin (T 30).

DETAILED DESCRIPTION OF EXEMPLARY EMBODIMENTS

EXAMPLES

Figure 1:
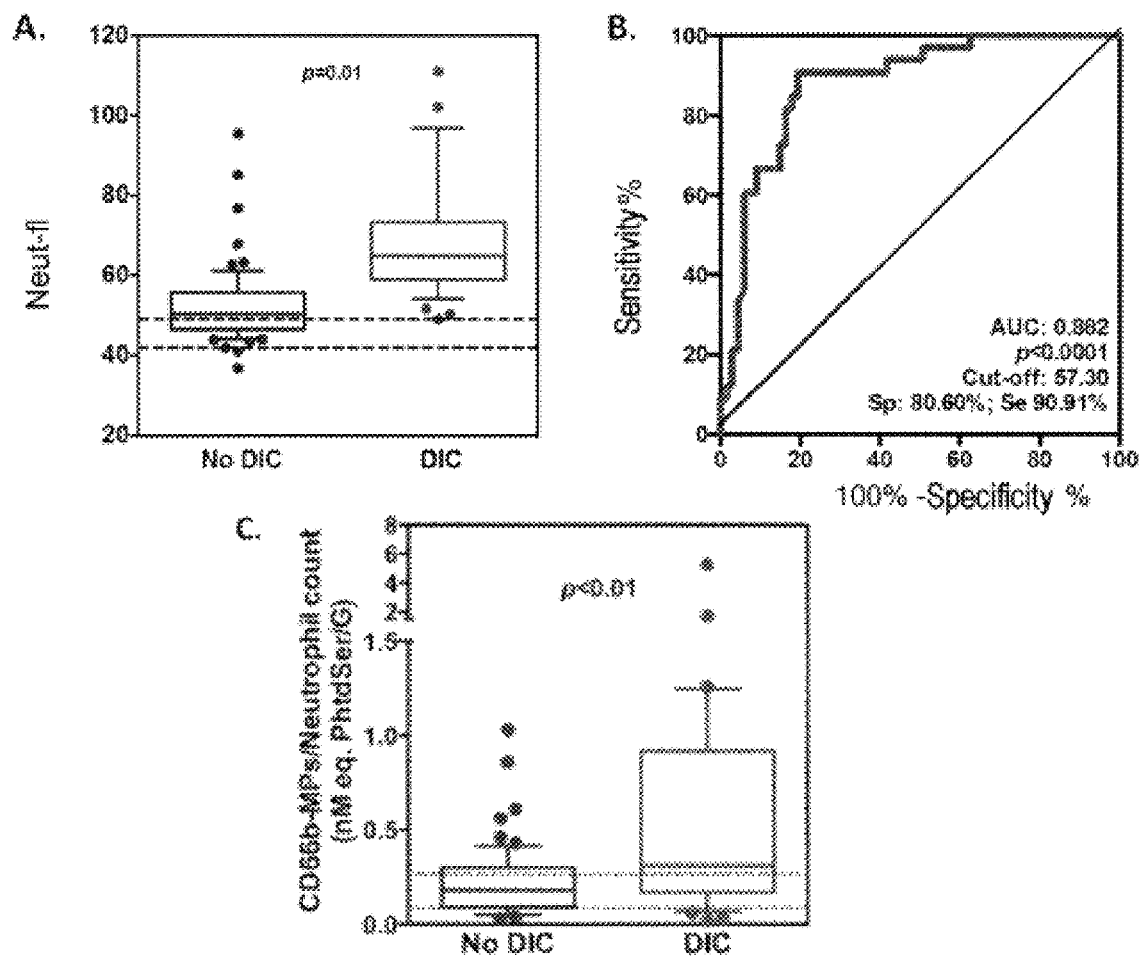
FIG. 1 represents a high fluorescence of polynuclear neutrophils (PNN) (NEUT-FL) that is significantly associated with DIC. The results are represented by red (DIC) or blue (absence of DIC) box-and-whisker plots. The horizontal line within the box corresponds to the median. The upper and lower limits of the box correspond to the 25th and 75th percentiles, respectively, and the uppers and lower bars to the 10th and 90th percentiles. The dashed lines correspond to reference values. Statistical analyses represent the differences between the repeated measurements between patients with or without DIC. A. NEUT-FL in 100 patients in septic shock. B. ROC (Receiver-operating characteristic) curve of NEUT-FL during septic shock. C. Neutrophil-based microparticles related to the neutrophil count in 100 patients in septic shock.
Figure 2:
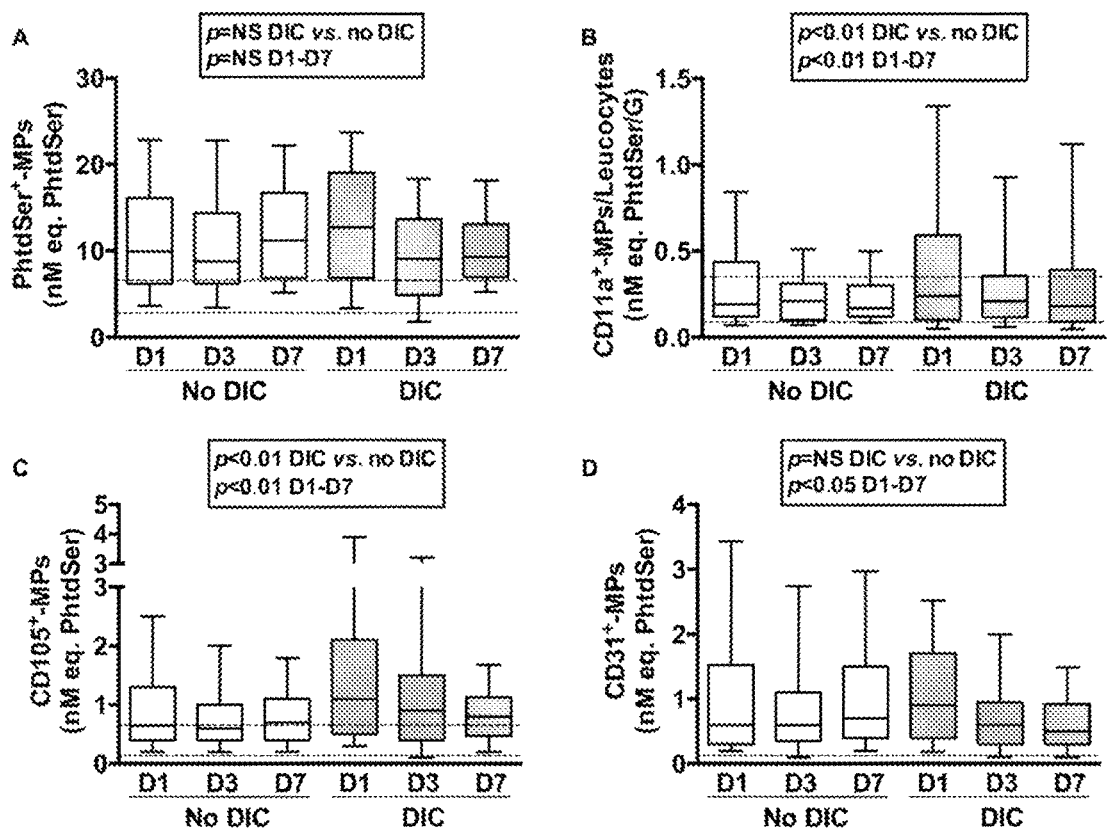
FIG. 2 represents a box plot of the mean concentration of the plasma membrane microparticles as phosphatidylserine equivalent (y-axis) as a function of time during DIC (gray) or not during DIC (white). The dashed lines represent normal values. Statistical analyses represent the differences of the repeated measurements between the subjects with or without DIC as a function of time.
Figure 3:
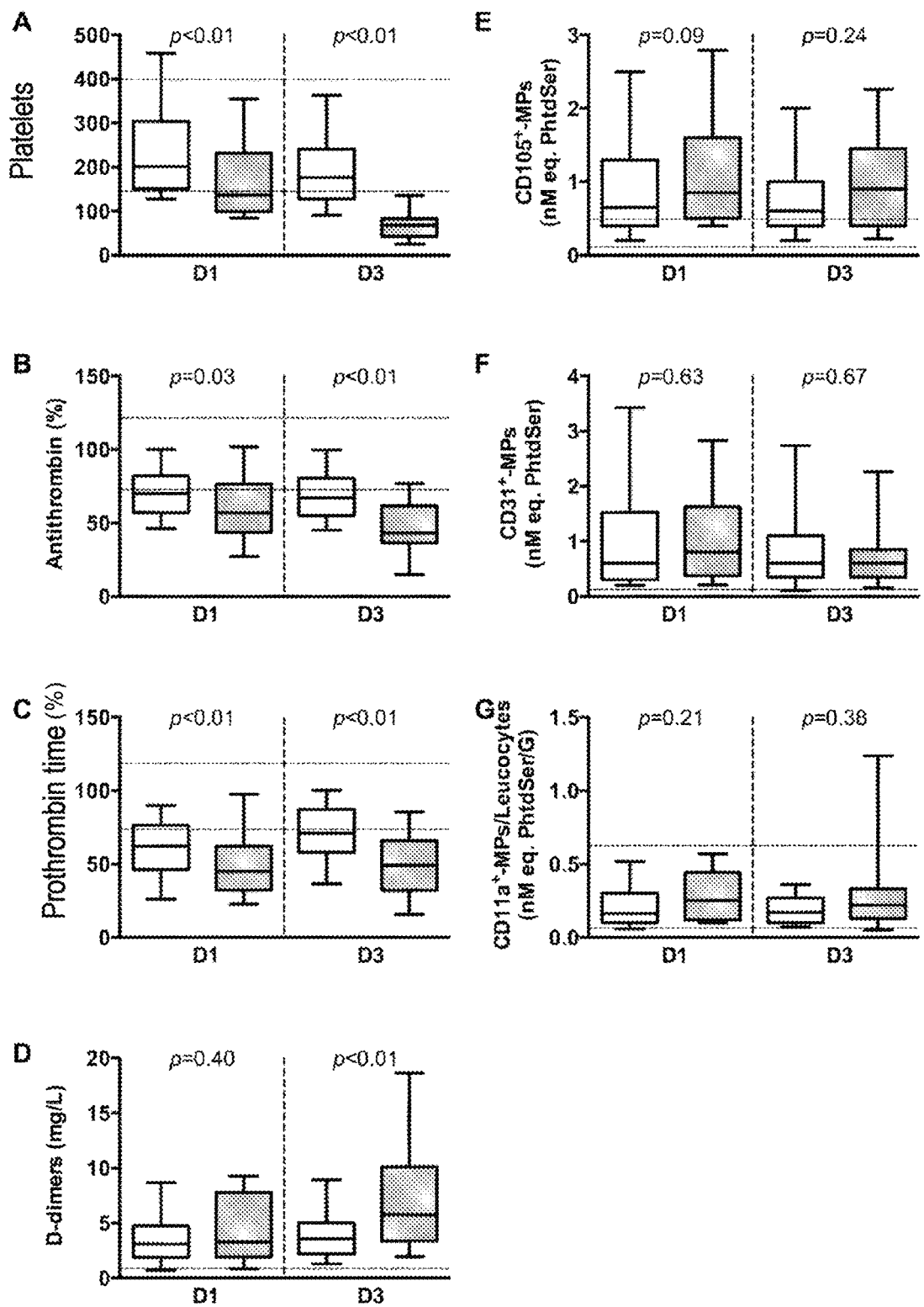
FIG. 3 represents box plots of the results obtained as a function of the presence of DIC (gray) or no DIC (white). The dashed lines represent normal values. The y-axes represent the leukocyte concentration in g/l, platelet concentration in g/l, the ratio of membrane microparticles bearing CD11a to the leukocyte count in nM/g, the prothrombin level in %, the antithrombin level in %, the D-dimers concentration in mg/l, the contents of circulating CD105 microparticles and CD31 microparticles. The x-axes represent the condition and the day of measurement: 1st day (D1), 3rd day (D3). Statistical analyses represent the differences of the repeated measurements between the subjects with or without DIC as a function of time.
Figure 4A:
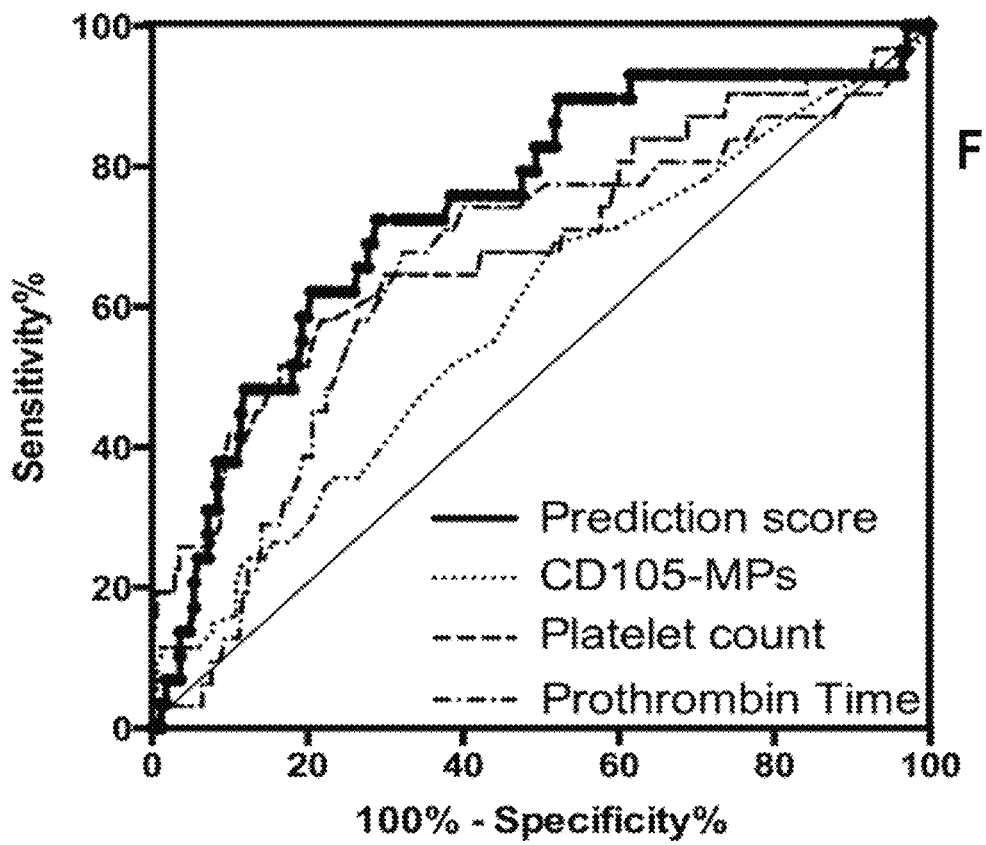
FIG. 4 represents, in A, the ROC curves for CD105-microparticles, prothrombin level, platelet count and predictive DIC score, and in B, the treatment options decision tree for patients. N+ relates to the number of patients with DIC, N− is the number of patients without DIC.
Figure 4B:
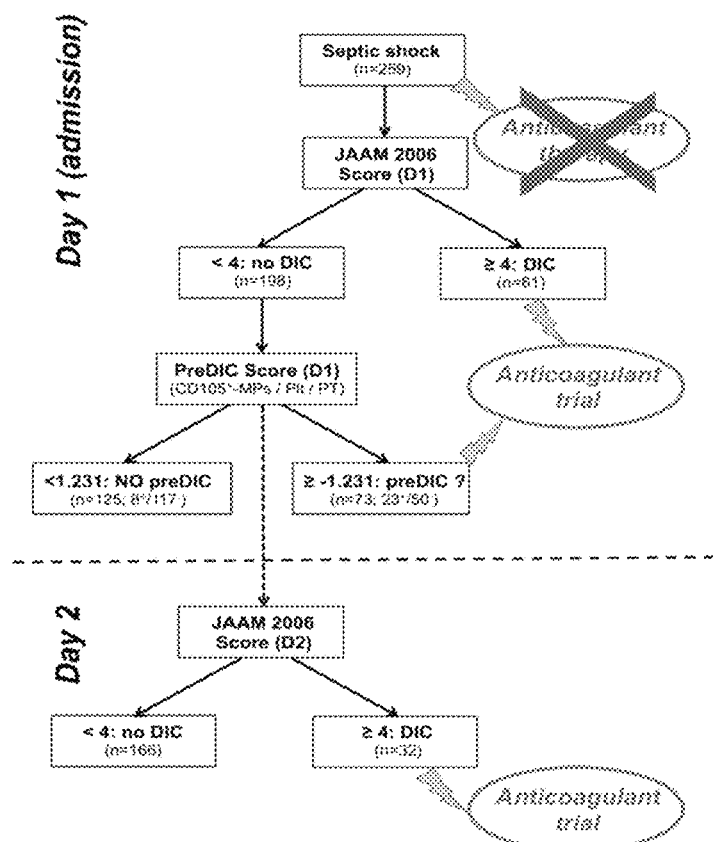

Example 1 Use of a Score Combining CD105+-MPs, Prothrombin Level and Platelet Count Summary Aims: the stratification of patients in septic shock is unsatisfactory and may lead to unsuitable treatment allocation in randomized clinical trials (RCTs), in particular regarding anticoagulant treatments. We show that the endothelium-derived microparticles CD105 are relevant biomarkers of disseminated intravascular coagulation (DIC) in septic shock. Prospective observational study in hospitalized patients in septic shock in four resuscitation units.

Patients and methods: 256 patients suffering from septic shock hospitalized consecutively, DIC was diagnosed according to the JAAM 2006 score.

Main results: 259 patients were analyzed. 61 had DIC on admission (DIC-D1) and 32 developed DIC during the first 24 hours following admission (DIC-D2). Several logistic regression models confirmed that the endothelial cell-derived MPs were associated with DIC: CD105+-MPs (OR 2.13) and CD31+-MPs (OR 0.65) (p<0.05). In addition, the ratio of CD11a-microparticles to leukocytes is evidence of activation of the leukocytes (OR 1.59, p<0.05). The DIC prediction was also analyzed after excluding the DIC-D1 patients. A new analysis by multiple logistic regression demonstrated the association of CD105-MPs (>0.60 nM eq. PhtdSer, OR 1.67, p<0.01), platelet count (≤127 g/l or 0.99, p<0.01) and the prothrombin time (558%, OR 0.98, p<0.05) with DIC. A score combining these markers on admission predicts the absence of DIC (AUC 72.9%, specificity of 71.2%, sensitivity of 71.0%, with a negative predictive value of 93.1% and a positive predictive value of 31.0%).

Patients and Methods:

Patients 250 consecutive patients aged from 18 to 85 years were included. All patients met the criteria for septic shock on admission. According to the JAAM 2006 score[10], 40% of the patients have early DIC, defined by a JAAM score 24 on D1 or on D2. The characteristics of the patients are summarized in table 1. The patients with DIC were more severely ill, with statistically higher SOFA (Sequential Organ Failure Assessment Score) and SAPS2 (Simplified Acute Physiology Score) severity scores, and also higher mortality, in the DIC group. The platelet counts and neutrophil counts are significantly different between the two groups.

TABLE 1

Characteristics of the patients

| | Total (259) | CIVD (−) (166) | CIVD (+) (93) | p value |
|---|---|---|---|---|
| Characteristics | | | | |
| Males - N (%) | 162 (62.5) | 106 (63.9) | 56 (60.2) | 0.561 |
| Age - years | 66.8 ± 13.3 | 67.2 ± 13.6 | 66.1 ± 12.8 | 0.523 |
| SAPS II | 57.1 ± 19.0 | 52.9 ± 17.1 | 64.6 ± 19.9 | <0.001 |
| Mortality, day 28 - N (%) | 89 (34.4) | 47 (28.3) | 42 (45.2) | <0.001 |
| Organ affected | | | | |
| SOFA on admission | 11.3 ± 3.1 | 10.2 ± 2.8 | 13.2 ± 2.6 | <0.001 |
| Respiratory disorders - N (%) | 221 (85.3) | 137 (82.5) | 84 (90.3) | 0.089 |
| Acute renal impairment - N (%) | 144 (55.6) | 69 (41.6) | 75 (80.6) | <0.001 |
| Hepatic impairment - N (%) | 47 (18.1) | 19 (11.4) | 28 (30.1) | <0.001 |
| Location of infection | | | | 0.589 |
| Lungs | 100 (38.6) | 65 (39.2) | 35 (37.5) | — |
| Urinary | 28 (10.8) | 17 (10.2) | 11 (11.8) | — |
| Abdominal | 27 (10.4) | 13 (7.8) | 14 (15.1) | — |
| Bacteremia | 54 (20.8) | 32 (19.3) | 22 (23.7) | — |
| Unknown | 34 (13.1) | 22 (13.2) | 12 (13.0) | — |
| Treatment | | | | |
| Extrarenal purification - N (%) | 89 (34.4) | 40 (24.1) | 49 (52.7) | <0.001 |
| Adrenaline - N (%) | 43 (16.6) | 15 (9.0) | 28 (30.4) | <0.001 |

TABLE 1-continued

Characteristics of the patients

|  | Total (259) | CIVD (−) (166) | CIVD (+) (93) | p value |
|---|---|---|---|---|
| Fresh frozen plasma - N (%) | 26 (10.0) | 7 (4.2) | 19 (20.4) | <0.001 |
| Concentrated platelets - N (%) | 26 (10.0) | 4 (2.4) | 22 (23.7) | <0.001 |
| Heparin - N (%) | 191 (73.7) | 124 (74.7) | 67 (72.0) | 0.641 |
| HBPM - N (%) | 59 (22.8) | 44 (26.5) | 15 (16.1) | 0.056 |

Blood Sampling:

Tubes were taken for the analyses desired in this embodiment for treating the patients, including one EDTA tube (Vacutainer™, Becton Dickinson, Le Pont de Claix, France) used for carrying out the complete blood count and detection of fluorescence associated with DNA decompaction. Fifteen milliliters of blood were taken at the time of diagnosis of septic shock, then on the third day (D3) and seventh day (D7) on citrate tubes (0.109 M, Vacutainer™, Becton Dickinson, Le Pont de Claix, France) and dry tubes (Vacutainer™, Becton Dickinson, Le Pont de Claix, France). The tubes were immediately centrifuged twice at 2500 g for 15 minutes to obtain plasma depleted in platelets and serum and the samples are immediately frozen at −80° C. The blood samples were taken after putting in place an arterial catheter intended for the invasive monitoring of arterial pressure and for taking multiple blood samples, made desired in this embodiment by the patient's state, and did not lead to any additional punctures. There was no additional blood sample taken for the study. The most commonly used approach was via the radial artery. The six healthy volunteers had blood samples taken from a peripheral vein.

Blood Counts and Complete Blood Counts

The blood counts and complete blood counts were carried out by an automated flow cytometer (XN20 Sysmex© Corporation, Kobe, Japan) after conveying the blood tubes to the hematology laboratory using the customary internal hospital circuit for treating medical data. The complete blood counts were given from fluorescence channels and after labelling using 2 reactants (description according to Sysmex© Corporation): the first reactant lyses the red blood cells and acts on the leukocyte membranes by permeabilizing them. The second reactant, bound to a polymethine-based fluorochrome, binds to nucleic acids. This is a non-permeating agent applied after the cells have been fixed. The different leukocytes were then identified as a function of their fluorescence by side-scattered light and forward-scattered light sensors at a wavelength of 633 nm.

Hemostasis:

The hemostasis assessments were carried out on the STA-R (registered trademark) Evolution automated analyzer (Stago, Asnieres, France) using customary reactants. The prothrombin levels (TP), activated cephalin time (ACT), factor V level (FV), fibrinogen level, D-dimers (DD) and antithrombin (AT) were thus measured for each patient.

There is no "gold standard" for identifying DIC. We therefore decided to define the DIC diagnosis in accordance with the JAAM 2006 score[10]. Early DIC was defined by a JAAM (Japanese Association for Acute Medicine) score of greater than or equal to 4 during the first 48 hours of the shock.

TABLE 2

JAAM score: table according to Gando

| Biological parameters | JAAM |
|---|---|
| Systemic inflammatory response syndrome defined by meeting ≥ 2 of the following conditions temperature < 36° C. or > 38° C. heart rate > 90/min respiratory rate >20/min or PaCO2 <32 mm Hg leukocytosis > 12 000/mm³, <4000/mm³ or presence of circulating immature form (>10% of cells | [0] <3 [1] ≥3 |
| platelets (g/l) | [0] >120 [1] 80-119 or 30% [3] <80 or 50% |
| Prothrombin level (%) | [0] >64 [1] <64 |
| D-dimers (μg/ml) | [0] <5.0 [1] 5.0-15.0 [3] >15.0 |
| DIC diagnosis | Score ≥4/8 |

Microparticles Assay:

The pro-coagulant activity of the MPs was assayed by functional prothrombinase test on streptavidin-coated multiwell plate (Roche®, France) by capture on annexin V or by virtue of antibodies specific to the cellular origin for microparticle phenotyping. This was carried out at the different sampling times.

The method of functional assay of the MPs developed by the team uses a prothrombinase enzymatic test carried out on a multiwell plate. The assay is carried out after capture of the MPs on insolubilized biotinylated annexin V at the bottom of the streptavidin-coated wells. The test makes use of, on the one hand, the high affinity of annexin V (AV) for the phosphatidylserine (PhtdSer) expressed at the surface of the MPs, and on the other hand, the affinity of biotin for streptavidin. The streptavidin is covalently bonded to the bottom of the wells and the biotinylated AV attaches to the streptavidin. For the phenotyping of the MPs, the AV is replaced by different biotinylated monoclonal antibodies (Ab) specific to the different targets specific to the cellular origin of the MPs. Thus, we use an anti-CD105 Ab (endoglin)—(R&D Systems, Mineapolis, USA) to characterize the MPs of endothelial origin, an anti-CD11a Ab (Leinco Technologies, St Louis, USA) to characterize the MPs of leukocyte origin, and an anti-CD66b-CEACAM8-Ab (BD Pharmingen, Franklin Lakes, USA) to specifically characterize MPs of neutrophil origin. The standards for healthy volunteers were established in the course of previous studies (Stiel et al: "Neutrophil Fluorescence: A New Indicator of Cell Activation During Septic Shock-Induced Disseminated Intravascular Coagulation." Crit Care Med. 2016; 44(11): e1132-e1136).

The plasma samples (100 μl/well) containing the microparticles were then deposited in duplicate in the wells and incubated for 30 minutes at 37° C. After capture of the MPs at the bottom of the wells and extensive washing, the prothrombinase enzymatic reaction was carried out. The amounts of calcium and the coagulation factors II, Va and Xa added were determined such that the phosphatidylserine fixed to the MPs was the factor limiting the conversion of thrombin into prothrombin. The amount of thrombin generated was revealed by its lytic action on a chromogenic substrate (pNAPEP0216, 1.52 mM, Cryopep, Montpellier, France). The absorbance was measured using a spectrophotometer (VersaMax Molecular Devices, Sunnylavale, California, USA) at a wavelength of 405 nm. The absorbance measured is proportional to the amount of PhtdSer exposed by the MPs. The results are expressed as nanomolar of phosphatidylserine equivalent (nM eq. PhtdSer) by referring to a calibration curve produced with synthetic vesicles with known amounts of PhtdSer.

Statistics

The variables were described as frequencies and the comparison was made by a $\chi^2$ test or a Fisher's exact test. The quantitative data were given as means and standard deviations and analysed with the Kruskall-Wallis test. The repeated measurements were analyzed by repeated measures ANOVA or with a mixed linear model. The post-hoc analyses were carried out using the t-test with Bonferroni correction for the multiple comparisons. Before carrying out this analysis, the variables were assessed for normality and the variables for which the distribution is not normal were converted using either logarithmic, square root, inverse or exponential conversion. Several models of logistic regression were employed to explain the occurrence of DIC. All statistical analyses were performed with the R version 3.1.3 software (R Core Team (2012). R: A language and environment for statistical computing. R Foundation for Statistical Computing, Vienna, Austria.Rproject.org). A value of $p<0.05$ was considered to be statistically significant.

Main results: 259 patients were analyzed. 61 had DIC on admission (DIC-D1) and 32 developed DIC during the first 24 hours following admission (DIC-D2). Several logistic regression models confirmed that the endothelial cell-derived MPs were associated with DIC: CD105+-MPs (OR 2.13) and CD31+-MPs (OR 0.65) (p<0.05). In addition, the ratio of CD11a-microparticles to leukocytes is evidence of activation of the leukocytes (OR 1.59, p<0.05). The DIC prediction was also analyzed after excluding the DIC-D1 patients. A new analysis by multiple logistic regression demonstrated the association of CD105-MPs (>0.60 nM eq. PhtdSer, OR 1.67, p<0.01), platelet count (5127 g/l OR 0.99, p<0.01) and the prothrombin time (558%, OR 0.98, p<0.05) with DIC. A score combining these markers on admission predicts the absence of DIC (AUC 72.9%, specificity of 71.2%, sensitivity of 71.0%, with a negative predictive value of 93.1% and a positive predictive value of 31.0%).

Detailed Results

In order to analyze patients during admission, in order to assess the DIC prediction at D2 (DIC-D2), we excluded the DIC-D1 patients. These eighty eight patients were analyzed. The platelet count and the prothrombin level were significantly lower in DIC-D2 patients than in patients without DIC. Antithrombin and D-dimers did not differ. On D2 and D3, the platelet count, prothrombin level and antithrombin were lower than D1 in DIC-D2 patients and D-dimers were significantly higher (p<0.05). All these parameters are significantly different in patients without DIC (p<0.05), with a large increase for all three parameters. It should be noted that the ISTH "overt" and ISTH "non-overt" scores do not make it possible to predict DIC.

Microparticles, Early Markers of DIC

The circulating levels of total microparticles (MPs) are high in patients in septic shock. Cellular activation precedes DIC: in order to improve or enhance diagnosis of DIC on D2, from the point at which the patient is admitted to resuscitation, we analyzed endothelial microparticles and leukocyte activation.

CD105+-MPs (p=0.09) and CD11a+-MPs/leukocytes (p=0.18) were associated with DIC-D2, whereas this is not the case for CD31+-MPs.

Univariate analysis carried out on the biological indicators of DIC evaluated on D1, including routine and microparticle tests, revealed four parameters with p<0.20: CD105+-MPs, the platelet count, prothrombin level and also neutrophil fluorescence (NEUT-FL). CD105-MPs, the prothrombin level and the platelet count were significantly associated with DIC in a multiple logistic regression.

The individual performance of each parameter is greatly increased by combining them. The prediction equation is written: $1.342+(0.515\times[\text{CD105}^+\text{-MPs}])-(0.012\times[\text{Plt}])-(0.018\times[\text{PT}])$ with [CD105$^+$-MPs] in nM eq. PtdSer, [Plt] in g/l and [PT] in percentage (%).

The area under the curve was 72.9% with 95% Cl [66.2 to 78.9](p<0.001). The threshold, Cut-off, was −1.231 with a specificity of 71.2% [63.7 to 77.9], a sensitivity of 71.0% [52.0 to 85.8], a negative predictive value of 93.1% [72.5 to 99.6] and a positive predictive value of 31.0% [7.9 to 64.5].

In our cohort, 259 patients would have been admissible for a specific anticoagulant treatment established in earlier clinical trials. According to JAAM, 61 had DIC on admission and may immediately be admitted. The daily calculation of the JAAM score would make it possible to diagnose 31 other patients with DIC that are eligible for anticoagulant treatment, among the 198 remaining patients on day 2. Using our prediction score, 125 patients could be considered to be at a very low risk of DIC and could have not received an anticoagulant treatment. Only 8 (6.5%) will develop a DIP which would have been recognized by JAAM on day 2.

Microparticles, Early Markers of DIC

The circulating levels of total microparticles (MPs) were high in patients in septic shock. There is no quantitative difference between the MPs measured in the DIC group and in the non-DIC group. However, the patients with DIC exhibited a difference in terms of the phenotype of the plasma microparticles. The amount of endothelial CD105 MPs was greatly increased in patients with DIC compared to those that had not developed DIC (p<0.01). This difference was present from D1 and lasted up to D7. The leukocyte CD11a MPs, reflecting leukocyte activation, were significantly higher in patients with DIC from D1 to D7. Likewise, the ratio of leukocyte CD11a MPs/leukocytes was higher in patients who developed DIC (p<0.05). This difference was present from D1 and lasted (FIG. 1C). Likewise, there was a significant increase in neutrophil CD66b MPs in patients with DIC. The ratio of MPs-CD66b/neutrophils was increased in patients in septic shock and the difference between the two groups was found (p<0.01).

TABLE 3

| | Normal values | No DIC (N = 166) | "DIC-D 2" [a] (N = 32) | "DIC-D 1" [b] (N = 61) |
|---|---|---|---|---|
| DIC scores on admission (D 1) | | | | |
| Time on day 2 (hours) | | 16.9 [12.6-19.3] | 15.8 [12.9-18.7] | 16.7 [13.0-19.9] |
| JAAM 2006 | | | | |
| J 1 | <4 | 1.8 ± 0.7[#] | 2.4 ± 0.6[$] | 5.8 ± 1.6[#$] |
| D 2 | <4 | 1.6 ± 0.9[*#] | 5.0 ± 1.2* | 5.3 ± 2.0[#] |
| "Overt" ISTH 2001 | | | | |
| D 1 | <5 | 2.6 ± 1.1[#] | 3.0 ± 1.4[$] | 4.9 ± 1.2[#$] |
| D 2 | <5 | 3.0 ± 0.9[*#] | 4.6 ± 0.9* | 5.0 ± 1.3[#] |
| "Non-overt" ISTH 2001 | | | | |
| D 1 | <5 | 2.9 ± 1.4[*#] | 3.8 ± 1.3[*$] | 4.4 ± 1.1[#$] |
| D 2 | <5 | 2.6 ± 2.1[*#] | 5.0 ± 1.4* | 3.7 ± 2.3[#] |
| SIRS score > 3 | | 166 (100.0) | 32 (100.0) | 61 (100.0) |
| SOFA | | 10.2 ± 2.9[*#] | 12.3 ± 2.4* | 13.5 ± 2.8[#] |
| SAPS II | | 53.3 ± 18.0[*#] | 62.4 ± 19.9* | 63.5 ± 17.1[#] |
| Mortality at D 28 - N (%) | | 48 (28.3)[*#] | 13 (41.9)* | 29 (46.8)[#] |

[a] "DIC-D 2": patients exhibiting criteria for DIC on D 2 but not on D 1;
[b] "DIC-D 1": Patients exhibiting criteria for DIC on D 1
*$p < 0.05$ without DIC vs. DIC-D 2;
$p < 0$. without DIC vs. DIC-D 1;
$$p < 0.05$ DIC-D 1 vs. DIC-D 2

TABLE 4

Analysis by multiple logistic regression of the predictive value of the score for diagnosing DIC D2 patients (excluding DIC D1 patients).

| Parameter | Odds ratio | 95% CI | p | Cut-off | Sensitivity (%) | Specificity (%) |
|---|---|---|---|---|---|---|
| CD105+MPs | 1.67 | [1.20-2.33] | 0.002 | >0.6 nM eqPS | 71.70 | 48.19 |
| Platelet count | 0.99 | [0.98-0.99] | <0.001 | ≤127 g/l | 63.64 | 90.00 |
| Prothrombin level | 0.98 | [0.97-1.00] | 0.038 | ≤58% | 81.82 | 60.00 |

CD11a+-MPs/Leucocytes and antithrombin were not retained ($p > 0.25$)

Example 2 Example of a Score Combining Neutrophil Fluorescence, Prothrombin Level, Platelet Count and CD105-MP Microparticles.

Patients 150 consecutive patients of adult age, meeting all the criteria for septic shock on admission to intensive care, were included in the study. Patients suffering from terminal-stage chronic diseases and also patients suffering from neutropenia were excluded from the study. According to the JAAM score, 35% of the patients have DIC. The patients with early DIC induced by septic shock were more severely ill, with statistically higher SOFA (Sequential Organ Failure Assessment Score) and SAPS2 (Simplified Acute Physiology Score) severity scores, and also higher mortality, in the DIC group (table 5). The leukocyte and neutrophil counts were significantly lower in patients suffering from DIC, while the hemoglobin count and sodium level were unchanged, thereby excluding any plasma dilution effect.

Blood Sampling:

In addition to the samples presented in example 1, tubes were taken for the analyses desired in this embodiment for treating the patients, including one EDTA tube (Vacutainer™, Becton Dickinson, Le Pont de Claix, France) and used for the detection of fluorescence associated with DNA decompaction. Throughout the validation process, we analyzed, from samples taken from healthy volunteers, the ex vivo activation of neutrophils stimulated by a 4 µM concentration of ionomycin (Calbiochem, Merck Biodeveloppement, Martillac, France).

Blood Counts and Complete Blood Counts

The intensity of labelling with the DNA intercalator, which demonstrates the accessibility of the double strand (immature cell, cellular activation, etc.), has been identified as NEUT-FL. The standard for the NEUT-FL parameter was established from 1300 assessments, i.e. from all the adult patients having undergone a biological assessment for a period of 24 hours in Strasbourg CHU (university hospital) at the two hospitals sites that bring together all adult surgical and medical specialisms.

Analysis of the Morphology of the Cells

Blood smears were carried out on patients and sampled on EDTA (7.2 mg/4 ml)/citrate (0.129 M) tubes, then subjected to May-Grunwald Giemsa staining. Sampling of healthy volunteers was carried out from a blood sample taken from a peripheral vein.

Statistics:

The categorical (or qualitative) variables were analyzed by Fisher's exact test and the continuous variables were analyzed by the Wilcoxon signed-rank test. The normality of the distribution was analyzed by the Shapiro-Wilk test. The Bonferroni-Holm method was used to obtain adjusted p values for the multiple comparisons. The ROC (Receiver-operating characteristic) areas under the curves were analyzed and the Spearmann correlation coefficient was determined. A p value of less than 0.05 is considered to be statistically significant. All the statistical analyses were carried out by the R version 3.1.3 software (R Core Team (2012). R: A language and environment for statistical computing. R Foundation for Statistical Computing, Vienna, Austria.Rproject.org). The asymmetric variables are presented in the form of median values with interquartiles, by virtue of the GraphPad Prism® software version 6 (La Jolla, CA, USA).

Results:
Leukocyte counts The leukocyte and neutrophil counts were significantly lower in patients with DIC. Neutrophil fluorescence was increased in all patients in septic shock ($p<0.01$).

Cytomorphology of the Neutrophils

Figure 5:
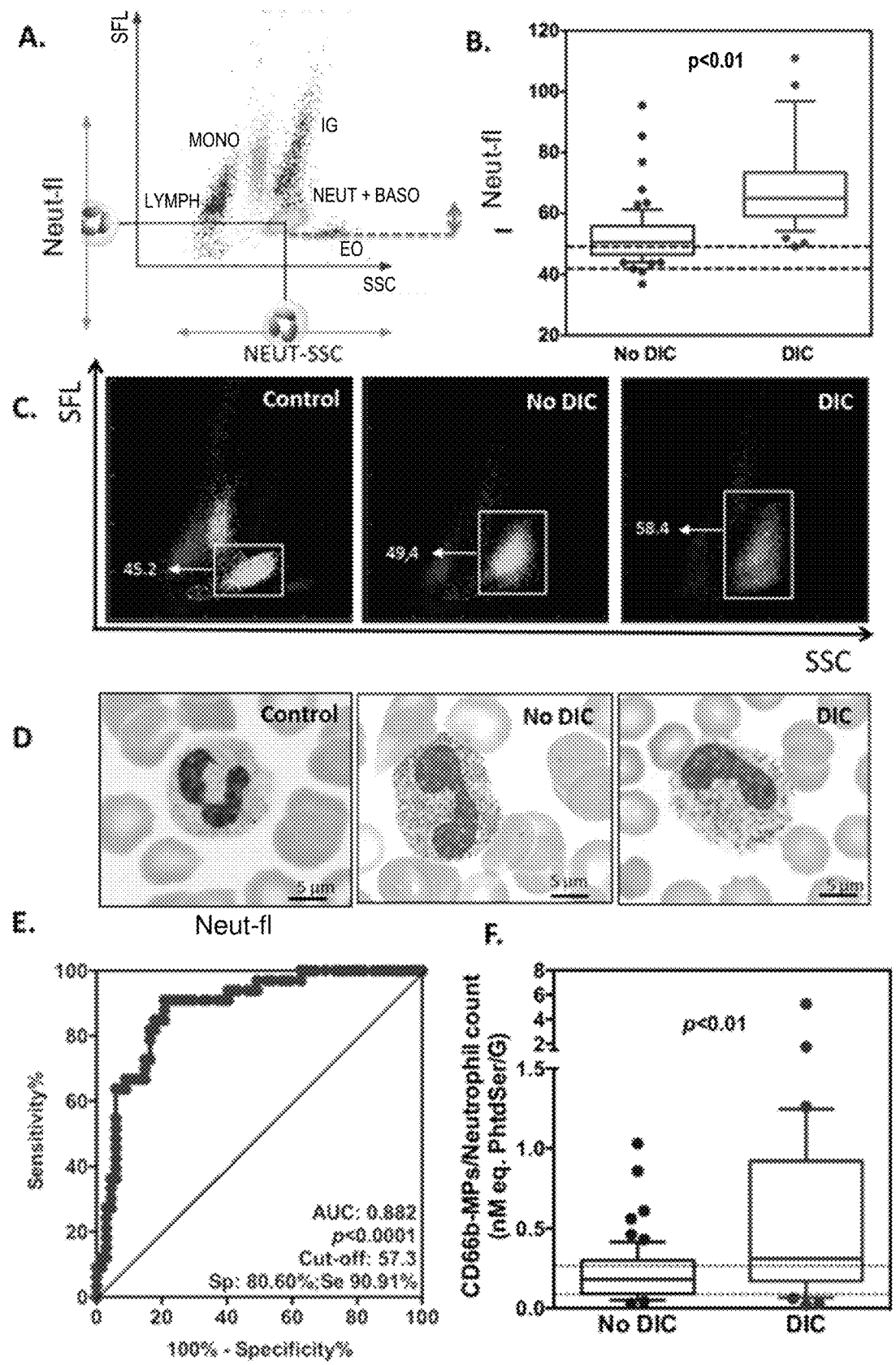
FIG. 5 is a supplement to FIG. 4, with, in A, the representation of the windows recorded by the automated cytometer and used for analysis of the parameter NEUT-FL. C represents variations of scattergrams in control subjects or subjects with sepsis, with or without DIC. D represents the morphological modifications observed on blood smears after MGG staining.

In the patients studied, it was observed that it is possible to associate DIC with an alteration in the morphology of the neutrophils observed from blood smears by May-Grunwald Giemsa staining as shown in FIG. 5D. Indeed, a reduction in the granularity and the lobulation of the nucleus in the neutrophils are especially observed. These alterations may be quantified by a cytological score with the aim of obtaining a positive and significant correlation ($p<0.05$) between its value and DIC over the first 3 days of sampling.

Leukocyte Fluorescence

The mean fluorescence of polynuclear neutrophils (PNN) measured in arbitrary units (AU) was significantly increased in patients with early DIC defined by a JAAM score 4 on D1 or D2 compared to the group without DIC, and the difference is significant ($p<0.01$): 70.0 [66.4-81.8] vs. 50.7 [46.3-53.8] AU, $p<0.05$, the normal values established in our laboratory from healthy volunteers being: 44.8 [43.5-46.9] AU, $p<0.05$ and the mean values measured in 1340 adult patients of the CHU, i.e. all patients that had a blood count over a period of 24 hours being: 46.80 [42.7-50.4] AU. An ROC curve was established: the area under the curve was 0.882 ($p<0.0001$) for the diagnosis of DIC with a cut-off at 57.3 AU, beyond which the increase in the fluorescence predicts a DIC with a sensitivity of 90.9% and a specificity of 80.6%.

Univariate analysis carried out on the biological indicators of DIC evaluated on D1, including routine and microparticle tests, revealed four parameters with $p<0.20$: $CD105^+$-MPs, the platelet count, prothrombin level and also neutrophil fluorescence (NEUT-FL).

TABLE 5

| Characteristics of the patients | | | |
|---|---|---|---|
|  | DIC | No DIC | p |
| SAPS 2 | 60.4 ± 15.2 | 52.7 ± 18.0 | 0.01 |
| SOFA | 12.5 ± 2.6 | 9.9 ± 3.2 | 0.01 |
| Mortality on day 7 - N (%) | 20.0 | 5.5 | 0.01 |
| Noradrenaline - N (%) | 35 (100.0) | 65 (100.0) | 1.00 |
| Dobutamine - N (%) | 7 (20.0) | 13 (17.8) | 1.00 |
| Mechanical ventilation - N (%) | 33 (94.3) | 61 (93.8) | 1.00 |
| Extrarenal purification - N (%) | 16 (45.7) | 19 (29.2) | 0.13 |
| JAAM 2006 | 4.6 ± 2.0 | 1.9 ± 0.7 | 0.01 |
| "Overt" ISTH 2001 | 4.4 ± 1.2 | 2.9 ± 1.0 | 0.01 |
| "Non-overt" ISTH 2001 | 4.6 ± 1.3 | 3.0 ± 1.3 | 0.05 |
| Prothrombin level (%) | 44 [33-62] | 64 [51-81] | 0.01 |
| D-dimers (μg/l) | 7.63 [3.01-20.00] | 3.31 [1.89-5.44] | 0.01 |
| Fibrinogen (g/l) | 5.58 [3.52-9.56] | 6.40 [4.67-7.68] | 0.03 |
| Leukocytes (g/l) | 10.3 [3.6-22.8] | 14.3 [11.6-20.1] | 0.05 |
| Neutrophil count (g/l) | 8.3 [4.0-19.9] | 14.0 [10.0-19.8] | 0.01 |
| Neutrophil fluorescence (AU) | 66.6 [59.3-80.4] | 50.0 [46.6-56.2] | 0.01 |
| Platelet count (g/l) | 80 [45-132] | 179 [140-190] | 0.05 |
| Hemoglobin (g/dl) | 10.5 [9.1-12.4] | 10.3 [9.6-12.1] | 0.35 |
| Proteins (g/l) | 52 [40-56] | 56 [48-64] | 0.43 |
| Sodium (mmol/l) | 136 [133-138] | 136 [132-140] | 1.00 |
| C-reactive protein (CRP) mg/l | 214 [84-282] | 173 [65-278] | 0.29 |

The multivariate analysis carried out on the biological parameters measured on D1 and eligible ($p<0.20$) during the above univariate analysis is described in table 6.

TABLE 6

| Multivariate analysis | | | |
|---|---|---|---|
| Parameters | Odds ratio | 95% confidence interval | p |
| Neutrophil fluorescence > 57 AU | 2.829 | 1.185 to 7.086 | 0.022 |
| $CD105^+$-MPs > 0.65 nM eq. PS | 2.343 | 1.289 to 5.236 | 0.017 |
| Platelet count < 127 g/l | 0.990 | 0.983 to 0.995 | <0.001 |
| Prothrombin level < 58.5% | 0.983 | 0.964 to 0.001 | 0.070 |

Application of the process for calculating the prediction score S1 from the following formula:

$$S_1 = 0.786 + 1.040 * V_{neutfl} + 0.851 * V_{CD105} + (-0.010 * V_{Plt}) + (-0.017 * V_{TP})$$

In which the value Vneutfl was equal to 1 if the fluorescence of the neutrophils in a plasma sample was greater than 57 AU, equal to 0 if the fluorescence of the neutrophils was less than or equal to 57 AU, a $V_{CD105}$ value equal to 1 if the $CD105^+$-MPs concentration was greater than 0.65 nM eq. PS or a $V_{CD105}$ value equal to 0 if the $CD105^+$-MPs concentration was less than 0.65 nM eq. PS, a $V_{Plt}$ value equal to 1 if the platelet concentration was less than 127 g/l or a $V_{Plt}$ value equal to 0 is the platelet concentration was greater than 127 g/l, a $V_{TP}$ value equal to 1 if the prothrombin level was less than 58.5% or a $V_{TP}$ value equal to 0 if the prothrombin level is greater than 58.5%.

An S value greater than −0.47 indicates DIC and/or the appearance of DIC.

The process was also carried out with the following prediction score:

$$S_1 = \varepsilon + V_{neutfl} \times \alpha + V_{CD105} \times \beta + V_{platelets} \times \Omega + V_{TP} \times \theta$$

wherein ε is from −0.708 to 2.280, α is from 0.152 to 1.928, β is from 0.154 to 1.549, 0 is from −0.016 to −0.005, and θ is from −0.036 to 0.001, This score was produced based on a 95% confidence interval of the different coefficients and makes it possible to determine the presence and/or appearance of DIC.

Example 3 Example of a Score Combining Neutrophil Fluorescence, Prothrombin Level, and Platelet Count In this example, the algorithm for detecting/predicting DIC was determined from clinical data obtained in the abovementioned example 2.

The construction of the algorithm was carried out by logistic regression modelling of early DIC in the cohort of patients from example 2: univariate then multivariate analysis for the variables significantly associated with the occurrence of early DIC, with p<0.20.

In this context, each patient was characterized by the measurement values for neutrophil fluorescence, prothrombin level and platelet count calculated according to the process described in example 2.

Application of the process for calculating the prediction score S2 from the following formula:

$$S_2 = 1.726 + 1.060 * V_{neufl} + (-0.010 * V_{Plt}) + (-0.022 * V_{TP})$$

Wherein the $V_{neufl}$ value was equal to 1 if the neutrophil fluorescence in a plasma sample was greater than 57 AU, equal to 0 if the neutrophil fluorescence was less than or equal to 57 AU, a $V_{Plt}$ value equal to 1 if the platelet concentration was less than 127 g/l or a $V_{Plt}$ value equal to 0 is the platelet concentration was greater than 127 g/1, a $V_{TP}$ value equal to 1 if the prothrombin level was less than 58.5% or a $V_{TP}$ value equal to 0 if the prothrombin level is greater than 58.5%.

An S value greater than 0.16 indicates DIC and/or the appearance of DIC.

The process was also carried out with the following S2 prediction score:

$$S_2 = \varepsilon + V_{neufl} \times \alpha + V_{Plt} \times \Omega + V_{TP} \times \theta$$

wherein ε is from 0.381 to 3.070, α is from 0.209 to 1.910, Ω is from −0.015 to −0.005, and 6 is from −0.040 to −0.004.

This score was produced based on a 95% confidence interval of the different coefficients and makes it possible to determine the presence and/or appearance of DIC.

Example 4 Identification of NET Markers Associated with Fluorescent Neutrophils by Flow Cytometry

Summary

Figure 6A:
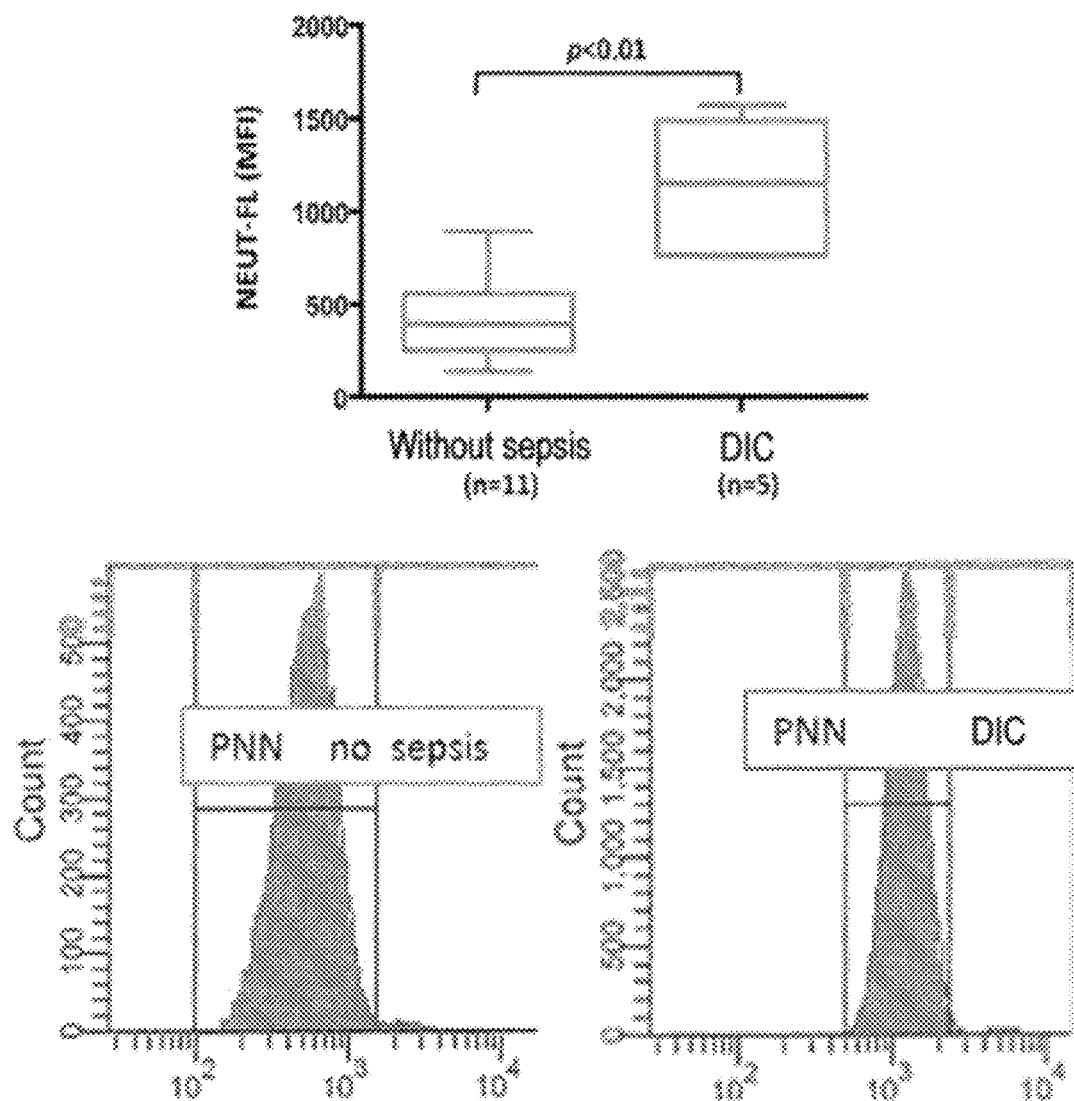
FIG. 6 represents the results obtained by conventional cytometry in the experiments described in example 4.
FIGS. 6B and 6C present scattergrams (SSC/FSC) of all the cells and the neutrophil fluorescence plots obtained after intracellular and extracellular labelling of the neutrophils for detection of NETs in the blood samples of non-septic subjects and after the triggering of NETosis by an exogenous agent (ionomycin). The two NETs markers studied are myeloperoxidase and citrullinated histones H3. P1, P2, P3 indicate sub-populations of neutrophils identified on the SSC and FSC scattergrams by virtue of the fluorescence signal associated with the labelling (corresponding colors between scattergrams and histograms).

Fluorescent neutrophils were identified by conventional flow cytometry using a labelling method similar to that described in example 2 above. The blood neutrophils were identified by a combination of fluorescent anti-leukocyte (pan-leukocyte marker CD45) antibodies, anti-polynuclear eosinophil (CD49d) antibodies and monocyte (CD14) antibodies. Labelling by nucleic intercalator was carried out after erythrocyte lysis. Acquisition in the 5 minutes following the labelling procedure made it possible to reveal a neutrophil population with greater fluorescence in the blood samples of patients with DIC compared to the patients without sepsis. (FIG. 6A)

Aims

Compare the presence of a population of neutrophils with significant fluorescence to the presence of NETs signifying NETosis, which may for example be associated with DIC. Blood samples from patients without sepsis, in which NETosis had been triggered by the addition of ionomycin (4 μM, 30 minutes at 37° C.), or from septic patients evaluated two NETs markers, respectively citrullinated histones H3 and myeloperoxidase activity by conventional flow cytometry were studied. Extracellular labellings, indicating the presence of antigens accessible to the cell surface and intracellular surface, after permeabilization, were carried out.

The materials and method are detailed below:

Blood sampling: Blood samples were taken in tubes using calcium heparinate as anti-coa. Stimulation by ionomycin (4 μM) of the samples from subjects without sepsis and with normal complete blood count was carried out for 30 minutes at 37° C. and at a final calcium concentration of 2 mM. For this purpose, 3.2 μl of ionomycin solution was introduced into 50 μl of blood sample. The ionomycin was then eliminated by low-speed centrifugation, namely at 540×g for 5 minutes.

Identification of the strongly fluorescing neutrophils: The blood samples were diluted in a phosphate buffer saline (PBS) 1× before incubation for 5 minutes with a combination of fluorescent pan-leukocyte antibodies (CD45-FITC), anti-polynuclear eosinophils (CD49d-PE) antibodies and anti-CD14-APC monocytes antibodeis from Biocytex, followed by erythrocyte lysis (slow lysis, Biocytex). A nucleic intercalator (SYTO 40, 1.33 mM or SYTO RNA Select, 133.5 μM, Thermofisher) was then applied 5 minutes before acquisition of the sample in a conventional cytometer (FacsCalibur, Becton Dickinson).

Identification of the NETs associated with neutrophils: The leukocytes, either stimulated or not stimulated by ionomycin, were labelled by incubation for 20 min at ambient temperature with a combination of antibodies: pan-leukocyte anti-CD45 clone H130 (V500, clone H130, BD biosciences), anti-neutrophil anti-CD16 clone 3G8 (BV421, BD biosciences), anti-MPO (clone 5B8, BD Biosciences) and anti-citrullinated histone (polyclonal antibody ab5103, Abcam). For this purpose, 50 μl of blood were incubated with the antibodies described above. The intracellular labelling was carried out after permeabilization (BD Facs Permeabilising solution diluted to ten-fold, BD biosciences). All the antibodies were incubated for 20 minutes at ambient temperature, namely 20° C., in darkness. After washing in PBS buffer containing 0.5% of FCS (fetal calf serum), a secondary rabbit anti-IgG antibody conjugated to Alexa 700 (A21038, Thermofischer) was incubated for 20 minutes at ambient temperature, namely 20° C., in darkness, to complete the secondary labelling of the anti-histone immunoglobulins. The acquisition of the samples in a conventional cytometer (Becton Dickinson) was carried out after washing in PBS buffer containing 0.5% FCS.

Figure 6B:
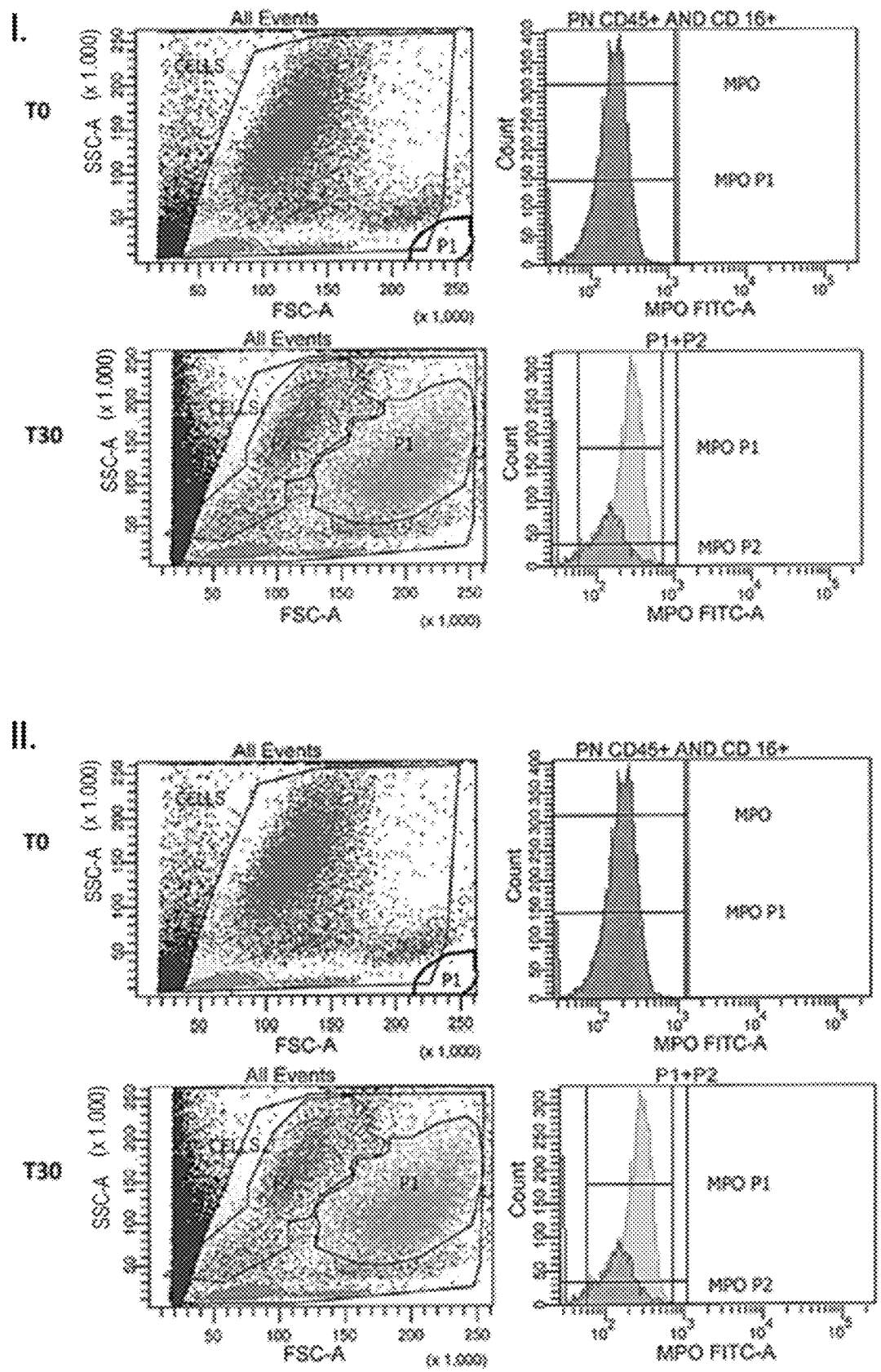
Figure 6C:
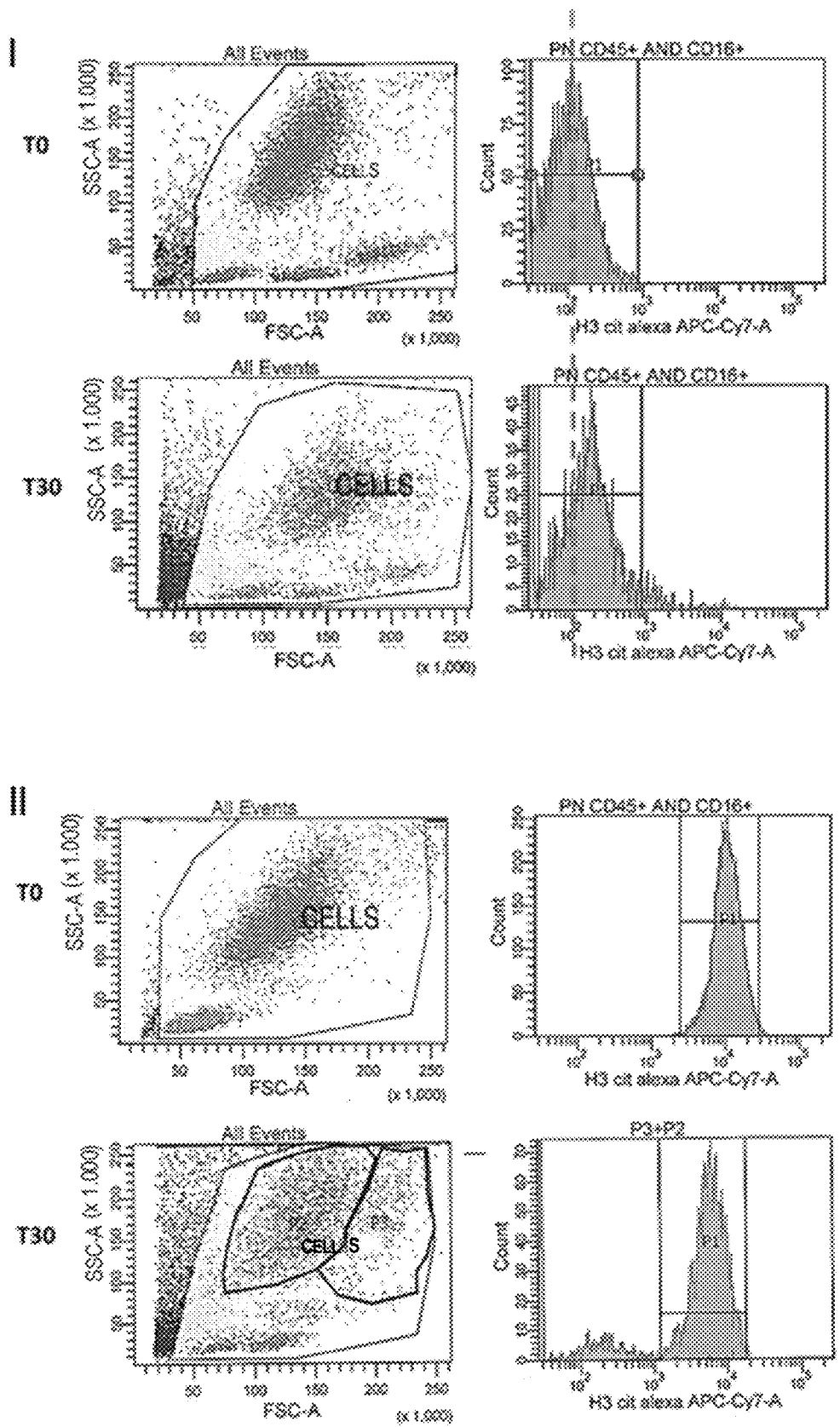

Main results: as shown in FIG. 6A, in the presence of DIC, the mean neutrophil fluorescence, expressed in arbitrary units, was significantly higher than that of the subjects not suffering from sepsis, using conventional cytometry (p<0.01). The extracellular and intracellular labellings by anti-citrullinated histone antibodies (FIG. 6C I and II, respectively) and anti-myeloperoxidase (FIG. 6B I and II, respectively) revealed that (i) NETosis is reflected by the appearance of larger neutrophils with (ii) an increased mean fluorescence after extracellular labelling by anti-citrullinated histone antibodies, while intracellular labelling decreases (iii) symmetrically, the mean fluorescence after extracellular labelling by anti-myeloperoxidase antibodies was greater in the large-sized neutrophil population while the mean intracellular fluorescence decreases.

These measurements clearly demonstrate that conventional flow cytometry makes it possible to identify increased neutrophil fluorescence in a sample from a DIC patient. In addition, this example clearly demonstrates that conventional flow cytometry makes it possible to identify neutrophil fluorescence, for example by probes for intercalating nucleic acids and also the presence of NETosis, for example triggered by an exogenous agent (ionomycin) or in a blood sample from a DIC patient by labelling citrullinated histones and myeloperoxidase in the neutrophil population.

REFERENCE LIST

1. Fourrier F. Severe sepsis, coagulation, and fibrinolysis: dead end or one way? Crit Care Med 2012; 40(9):2704-2708.
2. Gando S, Iba T, Eguchi Y, et al. A multicenter, prospective validation of disseminated intravascular coagulation diagnostic criteria for critically ill patients: comparing current criteria. Crit Care Med 2006; 34(3):625-631.
3. Taylor F B, Jr., Toh C H, Hoots W K, et al. Towards definition, clinical and laboratory criteria, and a scoring system for disseminated intravascular coagulation. Thromb Haemost 2001; 86(5):1327-1330.
4. Delabranche X, Boisrame-Helms J, Asfar P, et al. Microparticles are new biomarkers of septic shock-induced disseminated intravascular coagulopathy. Intensive Care Med 2013; 39(10):1695-1703.
5. Chung S, Kim J E, Park S, et al. Neutrophil and monocyte activation markers have prognostic impact in disseminated intravascular coagulation: in vitro effect of thrombin on monocyte CD163 shedding. Thromb Res 2011; 127(5):450-456.
6. Engelmann B, Massberg S. Thrombosis as an intravascular effector of innate immunity. Nature reviews Immunology 2013; 13(1):34-45.
7. Zonneveld R, Molema G, Plotz F B. Analyzing Neutrophil Morphology, Mechanics, and Motility in Sepsis: Options and Challenges for Novel Bedside Technologies. Crit Care Med 2015.
8. Matsumoto H. The technology of reagents in the automated hematology analyzers Sysmex XE-2100™—Red fluorescence technology. Sysmex J Int 1999; 9:179-185.
9. Park S H, Park C J, Lee B R, et al. Sepsis affects most routine and cell population data (CPD) obtained using the Sysmex XN-2000 blood cell analyzer: neutrophil-related CPD NE-SFL and NE-WY provide useful information for detecting sepsis. International journal of laboratory hematology 2015; 37(2):190-198.
10. Angus D C, van der Poll T. Severe sepsis and septic shock. N Engl J Med 2013; 369: 840-851.
11. Van der Poll T, Herwald H. The coagulation system and its function in early immune defense. Thromb Haemost. 2014; 112: 640-8.
12. Engelmann B, Massberg S. Thrombosis as an intravascular effector of innate immunity. Nat Rev Immunol. 2013; 13: 34-45.
13. Wada H, Matsumoto T, Yamashita Y. Diagnosis and treatment of disseminated intravascular coagulation (DIC) according to four DIC guidelines. J Intensive Care. 2014; 2: 15.
14. Gando S, Wada H, Thachil J, Scientific, Standardization Committee on DIC of the International Society on Thrombosis and Haemostasis. Differentiating disseminated intravascular coagulation (DIC) with the fibrinolytic phenotype from coagulopathy of trauma and acute coagulopathy of trauma-shock (COT/ACOTS). J Thromb Haemost. 2013; 11: 826-35.
15. Gando S, Otomo Y. Local hemostasis, immunothrombosis, and systemic disseminated intravascular coagulation in trauma and traumatic shock. Crit Care. 2015; 19: 72.
16. Fourrier F. Severe sepsis, coagulation, and fibrinolysis: dead end or one way? Crit Care Med. 2012; 40: 2704-8.
17. Levi M. The coagulant response in sepsis and inflammation. Hamostaseologie. 2010; 30: 10-2, 4-6.
18. Levi M, van der Poll T. Endothelial injury in sepsis. Intensive Care Med. 2013; 39: 1839-42.
19. Marshall J C. Why have clinical trials in sepsis failed? Trends Mol Med. 2014; 20: 195-203.
20. Meziani F, Delabranche X, Asfar P, et al. Bench-to-bedside review: circulating microparticles—a new player in sepsis? Crit Care. 2010; 14: 236.
21. Delabranche X, Boisrame-Helms J, Asfar P, et al. Microparticles are new biomarkers of septic shock-induced disseminated intravascular coagulopathy. Intensive Care Med. 2013; 39: 1695-703.
22. Levy M M, Fink M P, Marshall J C, et al. 2001 SCCM/ESICM/ACCP/ATS/SIS International Sepsis Definitions Conference. Intensive Care Med. 2003; 29: 530-8.
23. Taylor F B, Jr., Toh C H, Hoots W K, et al. Towards definition, clinical and laboratory criteria, and a scoring system for disseminated intravascular coagulation. Thromb Haemost. 2001; 86: 1327-30.
24. Gando S, Iba T, Eguchi Y, et al. A multicenter, prospective validation of disseminated intravascular coagulation diagnostic criteria for critically ill patients: comparing current criteria. Crit Care Med. 2006; 34: 625-31.
25. Hugel B, Zobairi F, Freyssinet J M. Measuring circulating cell-derived microparticles. J Thromb Haemost. 2004; 2: 1846-7. 22
26. Spero J A, Lewis J H, Hasiba U. Disseminated intravascular coagulation. Findings in 346 patients. Thromb Haemost 1980; 43: 28-33.
27. Dellinger R P, Levy M M, Rhodes A, et al. Surviving sepsis campaign: international guidelines for management of severe sepsis and septic shock: 2012. Crit Care Med. 2013; 41: 580-637.
28. Tagami T, Matsui H, Horiguchi H, et al. Antithrombin and mortality in severe pneumonia patients with sepsis-associated disseminated intravascular coagulation: an observational nationwide study. J Thromb Haemost. 2014; 12: 1470-9.
29. Gando S, Saitoh D, Ogura H, et al. A multicenter, prospective validation study of the Japanese Association for Acute Medicine disseminated intravascular coagulation scoring system in patients with severe sepsis. Crit Care. 2013; 17: R111.
30. de Stoppelaar S F, van't Veer C, van der Poll T. The role of platelets in sepsis. Thromb Haemost. 2014; 112: 666-77.
31. Hamzeh-Cognasse H, Damien P, Chabert A, et al. Platelets and infections—complex interactions with bacteria. Front Immunol. 2015; 6: 82.
32. Aupeix K, Hugel B, Martin T, et al. The significance of shed membrane particles during programmed cell death in vitro, and in vivo, in HIV-1 infection. J Clin Invest. 1997; 99: 1546-54.
33. Lacroix R, Robert S, Poncelet P, et al. Overcoming limitations of microparticle measurement by flow cytometry. Semin Thromb Hemost. 2010; 36: 807-18.
34. Robert S, Lacroix R, Poncelet P, et al. High-sensitivity flow cytometry provides access to standardized measurement of small-size microparticles—brief report. Arterioscler Thromb Vasc Biol. 2012; 32: 1054-8.
35. Lacroix R, Judicone C, Mooberry M, Boucekine M, Key N S, Dignat-George F, The ISSCW. Standardization of pre-analytical variables in plasma microparticle determination: results of the International Society on Thrombosis and Haemostasis SSC Collaborative workshop. J Thromb Haemost. 2013; 11: 1190-3.
36. Brenner T, Schmidt K, Delang M, et al. Viscoelastic and aggregometric point-of-care testing in patients with septic shock-cross-links between inflammation and haemostasis. Acta Anaesthesiol Scand 2012; 56: 1277-90.
37. Panigada M, Zacchetti L, L'Acqua C, et al. Assessment of fibrinolysis in sepsis patients with urokinase modified thromboelastography. PLoS One 2015; 10: e0136463.
38. Haase N, Ostrowski S R, Wetterslev J, et al. Thromboelastography in patients with severe sepsis: a prospective cohort study. Intensive Care Med 2015; 41: 77-85. 23

The invention claimed is:

1. An in-vitro process for predicting and/or detecting disseminated intravascular coagulation (DIC) in humans from a first biological sample that includes neutrophilse, wherein a measurement of fluorescence, of the neutrophils, predicts and/or detects DIC, and the measurement of fluorescence, of the neutrophils, is carried out using a DNA intercalating fluorochrome, the process comprising:
   obtaining the first biological sample from a patient, the first biological sample including the neutrophilse;
   applying DNA intercalating fluorochrome to the neutrophils, such that the DNA intercalating fluorochrome attaches to the neutrophils;
   performing a measurement of fluorescence of the neutrophils, with DNA intercalating fluorochrome attached thereto, of the first biological sample, so as to determine a measured value;
   comparing the measured value with a reference value;
   based on the comparing, generating a result, and the result being that the measured value exceeds the reference value;
   based on the result, generating a finding that the patient shows symptom of DIC; and
   based on the finding, administering a treatment to the patient, and the treatment being an anticoagulant treatment for DIC.

2. The detection process as claimed in claim 1, wherein: the performing a measurement, of fluorescence of the neutrophils, is performed using a flow cytometry process, with the assessment device being a flow cytometry device.

3. The detection process as claimed in claim 1, wherein the biological sample is a blood sample; and
   the obtaining the first biological sample includes taking the blood sample from the patient.

4. The process as claimed in claim 1, also including measurement, from a second biological sample, of the concentration $Rm_{CD105}$ of membrane microparticles bearing the cluster of differentiation 105 (CD105).

5. The process as claimed in claim 4, wherein the first and second biological samples are the same sample.

6. The process as claimed in claim 4, wherein the first and second biological samples originate from a patient with septic shock.

7. The process as claimed in claim 2, wherein the neutrophil fluorescence reference value is greater than 57 AU.

8. The process as claimed in claim 4, wherein the $Rm_{CD105}$ reference value is greater than 0.65 nM eq PS.

9. The detection process as claimed in claim 2, wherein the biological sample is a blood sample.

10. The process as claimed in claim 2, also including measurement, from a second biological sample, of the concentration $Rm_{CD105}$ of membrane microparticles bearing the cluster of differentiation 105 (CD105).

11. The process as claimed in claim 3, also including measurement, from a second biological sample, of the concentration $Rm_{CD105}$ of membrane microparticles bearing the cluster of differentiation 105 (CD105).

12. The process as claimed in claim 10, wherein the first and second biological samples are the same sample.

13. The process as claimed in claim 11, wherein the first and second biological samples are the same sample.

14. The process as claimed in claim 10, wherein the first and second biological samples originate from a patient with septic shock.

15. The process as claimed in claim 11, wherein the first and second biological samples originate from a patient with septic shock.

16. The process as claimed in claim 1, wherein the detected DIC has a sensitivity greater than or equal to 91% and a specificity greater than or equal to 81%.

* * * * *